(12) United States Patent
Tiwald

(10) Patent No.: US 7,110,912 B1
(45) Date of Patent: Sep. 19, 2006

(54) METHOD OF APPLYING PARAMETRIC OSCILLATORS TO MODEL DIELECTRIC FUNCTIONS

(75) Inventor: Thomas E. Tiwald, Lincoln, NE (US)

(73) Assignee: J.A. Woollam Co., INC, Lincoln, NE (US)

( * ) Notice: Subject to any disclaimer, the term of this patent is extended or adjusted under 35 U.S.C. 154(b) by 93 days.

(21) Appl. No.: 10/849,729

(22) Filed: May 20, 2004

Related U.S. Application Data

(60) Provisional application No. 60/471,753, filed on May 20, 2003.

(51) Int. Cl.
*G01B 7/02* (2006.01)

(52) U.S. Cl. .......................... 702/170; 703/2

(58) Field of Classification Search ............... 702/65, 702/66, 75, 90, 97, 99, 170, 188, 189, 194; 703/2; 712/207; 356/445, 631
See application file for complete search history.

(56) References Cited

U.S. PATENT DOCUMENTS

| | | | | |
|---|---|---|---|---|
| 4,905,170 A | * | 2/1990 | Forouhi et al. | 356/631 |
| 5,403,433 A | * | 4/1995 | Morrison et al. | 216/60 |
| 5,796,983 A | * | 8/1998 | Herzinger et al. | 703/2 |
| 6,485,872 B1 | * | 11/2002 | Rosenthal et al. | 430/30 |
| 6,654,873 B1 | * | 11/2003 | Kadowaki | 712/207 |
| 6,819,845 B1 | * | 11/2004 | Lee et al. | 385/122 |
| 6,862,095 B1 | * | 3/2005 | Horie | 356/445 |

* cited by examiner

*Primary Examiner*—Hal Wachsman
*Assistant Examiner*—Mohamed Charioui
(74) *Attorney, Agent, or Firm*—James D. Welch

(57) ABSTRACT

Methodology for segmentally modeling Real and Imaginary Parts of Optical Constants or Dielectric Functions using Kroneig-Kramer (K-K) Consistant Oscillators with substantially definite start and end points.

41 Claims, 12 Drawing Sheets

METHOD OF APPLYING PARAMETRIC OSCILLATORS TO MODEL DIELECTRIC FUNCTIONS

This Application claims benefit of Provisional Application Ser. No. 60/471,753 Filed May 20, 2003.

TECHNICAL FIELD

The present invention comprises methodology for modeling data, and more particularly a method for segmentally modeling Real and Imaginary Parts of Optical Constants or Dielectric Functions using Kramers-Kronig (K-K) Consistant Oscillators that have substantially definite start and end points.

BACKGROUND

Empirical investigation of substrate systems allows determination of the thicknesses of, and associated optical property component values, (eg. refractive index (n) and extinction coefficient (k), or mathematically equivalent real (e1) and imaginary (e2) complex dielectric function values), for films thereon.

Optical property component values for substrate systems can be empirically obtained by many methods, such as those utilizing substrate system film effected changes caused in reflected and/or transmitted light beam intensities, and those utilizing substrate system film effected changes in ellipsometric PSI and DELTA values. However obtained, resulting optical property component values, when plotted as a function of the wavelength, (ie. photon energy, which comprises of a beam of electromagnetic radiation utilized in the investigation), typically present as a rather irregular plot, which irregular plot can not be accurately represented by a simple analytical mathematical function over the range of wavelengths, (ie. photon energies), typically of interest, (eg. zero (0.0) ev to six (6.0) ev, and above).

To understand the present invention, it is helpful to realize that the index of refraction of a substrate system film represents the ratio of the speed electromagnetic radiation traveling in vacuum to that in said film material, and that it is typically a complex number, (N=n+ik), where N is the Index of Refraction, n is termed the refractive index and k is termed the extinction coefficient. An alternative representation can be arrived at by the relation (e=N^2), and is termed the Dielectric Function, (ie. e=e1+ie2), where (e1=n^2−k^2) and (e2=2×n×k). It is also noted that the photon energy of a beam of electromagnetic radiation is related to the frequency thereof by the equation (E=h×F), where E is energy, (typically in electron volts ev), h is Plank's Constant, and F is Frequency. As well, Frequency, in electromagnetic radiation, is related to Wavelength by the relationship (C=F×W), where C is the speed of light and W is wavelength, hence (E=h×C/W). In addition, electrical properties of a material are related to the optical properties by known relationships. For instance, electrical conductivity is found to be proportional to e2.

One approach to modeling the Imaginary Part (e2) of a Dielectric Function is to identify some number of points thereupon and fit a polynomial thereto. Applying a Kramer-Kronig (K-K) Integration to the Imaginary Part (e2) provides the Real Part (e1). This is discussed in an Article titled "High Precision UV-Visible-Near-IR Stokes Vector Spectroscopy", Zettler et al., Thin Solid Films, 234 (1993). It is also important to understand that the real and imaginary components of the Refractive Index (ie. n and k), are not independent of one another. As principal of causality applies, known as the Kramer-Kronig, (K-K), relationship, and theoretically, allows determining k(E) when n(E) is known, and vice-versa.

Continuing, other Dielectric Function Models have been developed for semiconductors. Adachi has developed a (K-K) consistent model suitable for below energy band-gap calculations that has been used to describe ternary alloys by interpolating parameters between binary endpoints, (see S. Adachi, "Optical dispersion relations for GaP, GaAs, GaSb, InAs InSb, Al(x)Ga(1−x)As, and In(1−x)As(y)P(1−y)", Appl. Phys., Vol 66, p. 6030, 1989. The ability to interpolate parameters produces much more physically realistic dielectric models than simply averaging dielectric functions of the end-point binary materials. For terniary alloy models, the strong Critical Point (CP) structure of semiconductors causes simple averaging schemes to produce doubled (CP) structures at the energies of binary endpoints, (see P. G. Snyder, J. A. Woollam, S. A. Alterovitz and B. Johs, "Modeling Al(x)Ga(1−x)As Optical Constants as Functions of Composition", J. Appl. Phys., Vol. 68, p. 5925, 1990). Forouhi and Bloomer have provided a dielectric model for semiconductors which is (K-K) consistent and has a very small set of coefficients, (see A. R. Forouhi and I. Bloomer, "Optical Properties of Crystaline Semiconductors and Dielectrics", Phys. Rev. B, vol. 38, p. 1865, 1988 and U.S. Pat. No. 4,905,170). The Forouhi and Bloomer model, however, has been found to have insufficient flexibility to fit existing dielectric functions accurately enough for ellipsometric modeling. Oscillator ensembles, (eg. harmonic and Lorentz), have been used to describe the above energy-gap behavior of some semiconductors and the AlGaAs alloy system, (see a paper by M. Erman, J. B. Theeten, P. Chambon, S. M. Kelso and D. E. Aspnes, titled "Optical Properties and Damage Analysis of GaAs Single Crystals partly Amorphised by ion Implantation", J. Appl. Phys. vol. 56, p. 2664, 1984; and a paper by H. D. Yao, P. G. Snyder and J. A. Woollam, titled "Temperature Dependence of Optical Properties of GaAs", J. Appl. Phys., vol. 70, p. 3261, 1991; and a paper by F. Terry Jr., "A Modified Harmonic Oscillator Approximation Scheme for the Dielectric Constants of Al(x)Ga(1−x)As", J. Appl., vol 70, p. 409, 1991). These models have been used to fit measured ellipsometric data, however, they are incapable of describing direct-energy-band-gap spectral regions, and they require extra fictitious oscillators to fill in the absorbtion between (CP's). Kim and Garland et al. have developed a (K-K) consistent model that can adequately describe a semiconductor dielectric function above, below and through the fundamental direct energy-gap, and this model has been applied to the AlGaAs alloy system, (see C. C. Kim, J. W. Garland, H. Abad and P. M. Raccah, "Modeling the Optical Dielectric Function of Semiconductors: Extension of the Critical-Point-Parabolic-Band Approximation", Phys Rev. B, vol 45, p. 11749, 1982; C. C. Kim, J. W. Garland, H. Abad and P. M. Raccah, "Modeling the Optical Dielectric Function of the Alloy System Al(x)Ga(1−x)As", Phys. Rev. B, vol. 47, p. 1876, 1993). This model can accurately describe the dielectric function and higher order derivatives. However, to determine required internal coefficients a two stage fitting process is used. First (CP) energies and broadening are determined by fitting derivatives of the dielectric function, and then the remaining internal coefficients are determined with the energies and broadenings fixed. It will be appreciated that this model then requires that the dielectric functions exist before the model can be fitted. Furthermore, attempts at fitting all coefficients simultaneously (as necessary for direct ellipsometer data fitting), are unlikely to succeed because of the highly correlated nature of the functions internal to the model. Over part of the spectral range, the modeled imaginary part of the dielectric function results from the difference of internal function values one-hundred (100) times larger than the final value. The internal coefficients are delicately balanced to produce the proper output, and small changes in (CP) energies can cause large deviations in the model output. In addition, Lorentzian Broadening, which is known to be wrong for elements and compounds, is utilized in by Kim & Garland et al. work. While the Kim & Garland et al. work is very interesting, there remained need for an improved Parametric Model such a that taught in U.S. Pat. No. 5,796,983, which is discussed in detail in the Disclosure and Detailed Description Sections of this Specification, along with other applicable Oscillator Structures, (eg. Gaussian, Narrow Lorentzian, Harmonic, TOLO, Ionic1, Ionic2). As demonstrated in the Detailed Description Section of this Specification, typical conventional practice is to place Oscillator Structures in a Plot of the Imaginary Part of the Dielectric Function (e2) such that at each wavelength the sum of the contributions results in said Imaginary Part. Typically this requires placing Oscillator Structures under peaks, and elsewhere, which placement is an acquired art.

Need remains for a simple mechanical approach to placing Oscillator Structures in a Plot of the Imaginary Part of the Dielectric Function (e2) such that summation of contributions thereof at each wavelength results in said Imaginary Part of the Dielectric Function (e2). Said approach should utilize (K-K) consistant Oscillator Structures so that the Real part of the Dielectric Function results from an integration procedure.

DISCLOSURE OF THE INVENTION

To begin, it is to be generally understood that the practice of ellipsometry involves causing polarized electromagnetic radiation to interact with a sample, and determining sample associated ellipsometric PSI ($\Psi$) and DELTA ($\Delta$) values, where PSI ($\Psi$) and DELTA ($\Delta$) are related by:

$$\rho = rp/rs = \text{Tan}(\Psi) \exp(i\Delta)$$

Ellipsometric PSI and DELTA correspond to change in a ratio of orthogonal beam components (typically (rp/rs) where "p" and "s" components are in a "p" plane defined by the beam and a perpendicular to the sample surface, and in an "s" plane perpedicular to said "p" plane and parallel to the sample surface), and change in phase between the "p" and "s" components respectively. Dielectric Functions for a sample, which consist of real (e1) and imaginary (e2) components, can be derived from ellipsometric PSI and DELTA values via a regression procedure.

It is noted that it is prefered practice to fit oscillator structures to the Imaginary Part (e2) of the Dielectric Function such that summation of contributions therefrom at each wavelength provide a fit. Typical practice is to position Oscillator Structure peaks under peaks in the (e2) plot. The disclosed invention breaks with that convention and simply places a plurality or multiplicity of typically, though not necessarily, similar oscillator structures at identified wavelength locations which do not necessarily have any definite relationship to the shape of the Dielectric Function. Some will be positioned so that their peaks are located near (e2) plot peaks, but most are not so positioned. The spacing of the oscillator structures under present invention teachings can be equal, or can be substantially random, or can involve more oscillator structures being placed in wavelength regions near peaks in the (e2) plot. Any functional arrangement is within the scope of the present invention, but the goal is not to model a plot with a minimum number of oscillator structures possible as is the goal in conventional procedures. Instead the goal is to make the procedure mechanical so that essentially anyone, regardless of training and experience, can practice it successfully after a very short period of instruction.

A disclosed invention method of segmentally modeling real and imaginary parts of dielectric functions with Kramers-Kronig (K-K) consistency, then comprises the steps of:

a) providing an imaginary part of a dielectric function and dividing it into a plurality of segments;

b) fitting each segment with an appropriate approximating K-K consistent mathematical construction, the mathematical constructions being continuous at intersection between adjacent segments, each mathematical construction comprising a selection from the group consisting of:

a mathematical equation; and a summation of oscillator structures.

Where a mathematical equation is fit to the imaginary imaginary part of a dielectric function it can be of a polynomial form of degree (n–1), where (n) is sum of the number of intersections between segments plus a beginning and an end node. It is disclosed, however, that the technique of fitting the imaginary part of a Dielectric Function with a polynomial of degree one less than the number of points being fit, (eg. a Cubic Spline as discussed in "Applied Numerical Methods for Digital Computation", James et al., Harper Row (1985)), is known, followed by applying a K-K Integration to provide the real part of the Dielectric Function. In contrast, the disclosed invention provides a separate mathematical construction for each segment between identified points.

A more relevant presently disclosed method of segmentally modeling real and imaginary parts of dielectric functions with Kramers-Kronig (K-K) consistency, then comprising the steps of:

a) providing an imaginary part of a dielectric function over spectroscopic range, and dividing said spectroscopic range into a plurality of segments;

b) fitting each said segment in said spectroscopic range with an approximating K-K consistent oscillator structure, said approximating oscillator structure in each said segment beginning and ending at the start and end of said respective segment, such that a summation of contributions from said oscillator structures present at each point within said spectroscopic range approximates said imaginary part of said dielectric function, and via Kramers-Kronig (K-K) consistency, also the real part of said dielectric function.

A specific embodiment of said more relevant method provides that the segments are of equal spectroscopic range lengths and at least one of said K-K consistent oscillator structures is preferably triangular shaped; the start and end of all oscillator structures, except the start of the first and end of the last, being positioned at the same spectroscopic point as are peaks of immediately adjacent oscillator structures.

Another specific embodiment of said more relevant method provides that at least one segment in said spectroscopic range is of a different length than other segments in said spectroscopic range and at least one of said K-K consistent oscillator structures is preferably triangular shaped; the start and end of all oscillator structures, except the start of the first and end of the last, being positioned at the same spectroscopic points as are peaks of immediately adjacent oscillator structures.

A more detailed disclosure of a present invention method of segmentally modeling real and imaginary parts of dielectric functions using Kramers-Kronig (K-K) consistent oscillators, comprises the steps of:

practicing steps a and b:

a) providing experimentally obtained data for real and imaginary parts of a dielectric function vs. wavelength for a sample comprising a transparent thin film on a substrate, over a determined range of wavelengths;

b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a global fitting procedure evaluating parameters, including the thickness of the transparent thin film and the location and amplitude of the pole in said mathematical model, utilizing the data corresponding to the real part of the dielectric function;

with transparent thin film thickness evaluated in step b, proceeding to practice steps c, d and e sequentially:

c) defining a wavelength range segment length such that the sum of (n+0.5) wavelength range segments exactly span the determined wavelength range, and beginning at one end of said determined wavelength range placing a (K-K) consistent oscillator which comprises an amplitude parameter and begins and ends at the extents of the first segment with its peak midway therebetween, then performing a point by point fit to the imaginary part of the dielectric function data over wavelengths in said first wavelength range segment such that (K-K) consistent oscillator defining parameters are evaluated;

d) placing a second (K-K) consistent oscillator which begins at a wavelength at which the first (K-K) consistent oscillator peaks and ends one wavelength range segment length therefrom and has a peak midway therebetween, then performing a point by point fit to the imaginary part of the dielectric function data over said first and second wavelength range segments such that (K-K) consistent oscillator defining parameters in said first (K-K) consistent oscillator are re-evaluated and oscillator defining parameters in said second (K-K) consistent oscillator are evaluated;

for each of the remaining (n–2) wavelength range segments, sequentially;

e) placing a (K-K) consistent oscillator which begins at a wavelength at which the just prior (K-K) consistent oscillator peaks and ends one wavelength range segment length therefrom and having a peak midway therebetween, then performing a point by point fit to the imaginary part of the dielectric function data over said wavelength range segments which are fitted with (K-K) consistent oscillators, such that oscillator defining parameters in previously evaluated (K-K) consistent oscillators are re-evaluated and oscillator defining parameters in the added oscillator are evaluated;

such that at each wavelength over the determined range of wavelengths the sum of the contributions of each evaluated (K-K) consistent oscillator approximates the magnitude of the imaginary part of the dielectric function.

The just recited method assumes use of equal length wavelength range segments, but said method of segmentally modeling real and imaginary parts of dielectric functions with Kramers-Kronig (K-K) consistent oscillators could involve utilizing variable length wavelength range segments, and comprise the steps of:

practicing steps a and b:

a) providing experimentally obtained data for real and imaginary parts of a dielectric function vs. wavelength for a sample comprising a transparent thin film on a substrate, over a determined range of wavelengths;

b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a global fitting procedure evaluating parameters, including the thickness of the transparent thin film and the location and amplitude of the pole in said mathematical model, utilizing the data corresponding to the real part of the dielectric function;

with transparent thin film thickness evaluated in step b, proceeding to practice steps c, d and e sequentially:

c) defining n wavelength range segment lengths such that the sum of said n wavelength range segments plus half the length of the last wavelength range segment at one end of said wavelength range exactly spans the determined wavelength range, and beginning at the opposite end of said determined wavelength range placing a (K-K) consistent oscillator which comprises an amplitude parameter and begins and ends at the extents of the first segment with its peak midway therebetween, then performing a point by point fit to the imaginary part of the dielectric function data over wavelengths in said first wavelength range segment such that (K-K) consistent oscillator defining parameters are evaluated;

d) placing a second (K-K) consistent oscillator which begins at a wavelength at which the first (K-K) consistent oscillator peaks and ends the second wavelength range segment length therefrom and has a peak midway therebetween, then performing a point by point fit to the imaginary part of the dielectric function data over said first and second wavelength range segments such that (K-K) consistent oscillator defining parameters in said first (K-K) consistent oscillator are re-evaluated and oscillator defining parameters in said second (K-K) consistent oscillator are evaluated;

for each of the remaining (n–2) wavelength range segments, sequentially;

e) placing a (K-K) consistent oscillator which begins at a wavelength at which the just prior (K-K) consistent oscillator peaks and ends at the nth wavelength range segment length therefrom and having a peak midway therebetween, then performing a point by point fit to the imaginary part of the dielectric function data over said wavelength range segments which are fitted with (K-K) consistent oscillators, such that oscillator defining parameters in previously evaluated (K-K) consistent oscillators are re-evaluated and oscillator defining parameters in the added oscillator are evaluated;

such that at each wavelength over the determined range of wavelengths the sum of the contributions of each evaluated (K-K) consistent oscillator approximates the magnitude of the imaginary part of the dielectric function.

In either of the embodiments recited above, said method can further comprise step f:

f) using starting values of parameters previously evaluated performing a global fitting procedure onto both real and imaginary parts of the dielectric function to re-evaluate parameters, including the thickness of the transparent thin film, the location and amplitude of the pole in said mathematical model, and the "N" (K-K) consistent oscillator defining parameters utilizing the data corresponding to the real and imaginary parts of the dielectric function, with a constraining limitation that said pole location is required to remain located at a wavelength beyond the lower wavelength, high energy, extent of said determined range of wavelengths.

It should be appreciated that in either version, the pole location and its amplitude at a wavelength beyond the lower wavelength, high energy, extent of said determined range of wavelengths, can be fixed during steps c, d and e, or the pole location and/or its amplitude can be re-evaluated along with previously evaluated oscillator defining parameters in previously evaluated (K-K) consistent oscillators during steps c, d and e, but wherein said pole location is required to remain located at a wavelength beyond the lower wavelength, high energy, extent of said determined range of wavelengths. The later constraint is necessary to prevent the Pole form entering large influence within the determined range of wavelengths. This is to be appreciated in the light that the purpose of said Pole is to provide a catch-all means to account for all influences beyond the determined range of wavelengths.

It is to be appreciated that the (K-K) consistent oscillators can be of a preferred tiangular shape, or each (K-K) consistent oscillator can be Gaussian or of a narrow Lorentzian shape, or constructed from at least one polynomial on at least one side of the peak value thereof.

In addition, said method, for each of the "n" the wavelength range segments, can involve letting the segment length thereof float and be fit along with other (K-K) consistent oscillator parameters.

Also, the global and point by point fits are based on a square error minimization criteria.

A modified method of segmentally modeling real and imaginary parts of dielectric functions with Kramers-Kronig (K-K) consistent oscillators, comprises the steps of:

practicing steps a and b:
a) providing experimentally obtained data for real and imaginary parts of a dielectric function vs. wavelength for a sample comprising a transparent thin film on a substrate, over a determined range of wavelengths;
b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a fitting procedure evaluating parameters, including the thickness of the transparent thin film and the location and amplitude of the pole in said mathematical model, utilizing the data corresponding to the real part of the dielectric function.

With transparent thin film thickness evaluated in step b, said modified method then proceeds to with steps c, d and e sequentially:
c) defining a wavelength range segment length such that the sum of (n) wavelength range segments exactly span the determined wavelength range, and beginning centrally in said determined wavelength range placing a first (K-K) consistent oscillator which comprises an amplitude parameter and begins and ends at the extents of the first segment with its peak midway therebetween;

for each of the remaining (n–1) wavelength range segments, on ether side of the central peak of the first (K-K) consistent oscillator;
d) placing a (K-K) consistent oscillator which begins at a wavelength at which the just centrally prior (K-K) consistent oscillator peaks and ends one wavelength range segment length therefrom and having a peak midway therebetween;
e) performing a fit to the imaginary part of the dielectric function data over said wavelength range segments which are fitted with (K-K) consistent oscillators, such that oscillator defining parameters in the (K-K) consistent oscillators are evaluated;

such that at each wavelength over the determined range of wavelengths the sum of the contributions of each evaluated (K-K) consistent oscillator approximates the magnitude of the imaginary part of the dielectric function.

The just recited modified method assumes that the wavelength range segment lengths are equal. Another modified method of segmentally modeling real and imaginary parts of dielectric functions with Kramers-Kronig (K-K) consistent oscillators allows for the wavelength range segments to vary, and comprises the steps of:

practicing steps a and b:
a) providing experimentally obtained data for real and imaginary parts of a dielectric function vs. wavelength for a sample comprising a transparent thin film on a substrate, over a determined range of wavelengths;
b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a fitting procedure evaluating parameters, including the thickness of the transparent thin film and the location and amplitude of the pole in said mathematical model, utilizing the data corresponding to the real part of the dielectric function;

with transparent thin film thickness evaluated in step b, proceeding to practice steps c, d and e sequentially:
c) defining (n) wavelength range segment lengths such that the sum of said (n) wavelength range segments exactly span the determined wavelength range, and beginning centrally in said determined wavelength range placing a first (K-K) consistent oscillator which comprises an amplitude parameter and begins and ends at the extents of the first segment with its peak midway therebetween;

for each of the remaining (n–1) wavelength range segments, on ether side of the central peak of the first (K-K) consistent oscillator;
d) placing a (K-K) consistent oscillator which begins at a wavelength at which the just centrally prior (K-K) consistent oscillator peaks and ends one wavelength range segment length therefrom and having a peak midway therebetween;
e) performing a fit to the imaginary part of the dielectric function data over said wavelength range segments which are fitted with (K-K) consistent oscillators, such that oscillator defining parameters in the (K-K) consistent oscillators are evaluated;

such that at each wavelength over the determined range of wavelengths the sum of the contributions of each evaluated (K-K) consistent oscillator approximates the magnitude of the imaginary part of the dielectric function.

It is noted that said alternative procedures could involve selecting the wavelength range segment length to be the entire wavelength range, and involve use of only one centrally placed oscillator. Further, it could involve use of three, or five etc. odd number oscillators. If fact, a procedure could be to begin with say one oscillator and perform a fit, and see if the fit is good enough. If not, additional wavelength range segments and oscillators can be added until a fit results in acceptable results.

The pole location and its amplitude at a wavelength beyond the lower wavelength, high energy, extent of said determined range of wavelengths can be fixed during step e, or the pole location and/or its amplitude are re-evaluated along with previously evaluated oscillator defining parameters in the (K-K) consistent oscillators during step e, but wherein said pole location is required to remain located at a wavelength beyond the lower wavelength, high energy, extent of said determined range of wavelengths.

The (K-K) consistent oscillators can be of tiangular shape, be constructed from at least one polynomial on at least one side of the peak value thereof, be of Gaussian, Narrow Lorentzian, Harmonic, TOLO, Ionic1, Ionic2 shape, or be of any functional shape or construction. (See the Detailed Description and Drawings of this Specification, and the J. A. Woollam WVASE Manual which is incorporated by reference herein, for insight to the various identified Oscillator structures).

It is again noted that the fits are preferably based on a square error minimization criteria such as, but not limited to, the Levenberg-Marquard approach.

Material Previously Disclosed in U.S. Pat. No. 5,796,983 Included to Provide Insight to Mathematical Constructions Comprising Non-Conventional Oscillator Structures U.S. Pat. No. 5,796,983 discloses that problem with prior modeling approaches which utilize the summation of the effects of a plurality of Oscillator Structures to provide approximate values for (e1) and/or (e2) as a function of photon energy, is that conventional Oscillator Structures do not provide accurate values of (e1) and/or (e2) at all values of photon energy. While a Lorentzian or Gaussian Oscillator Structure might be capable of providing a good (MSE) fit to a "Peak" region in a plot of (e2) with respect to photon energy, for instance, unless a "Tail" region projection from said "Peak" region in said plot is precisely Mathematically Lorentzian or Gaussian, data points removed from the region of the Peak will not be well approximated thereby. That is, the shape of the "Tail" regions of the Lorentzian or Gaussian Oscillator Structure is dictated by the shape of the peak region because of a limited number of degrees of freedom available. In some cases the sum of a plurality of Lorentzian or Gaussian Oscillator Structures centered at various central energies, with various amplitudes and broadenings can be utilized to provide improved fit over a range of photon energies. However, even where this approach is utilized, the lack of a sufficient number of degrees of freedom in an Oscillator Structure based Model to allow shaping the Peak region of an Oscillator Structure independently of the shape of the Tail regions, normally prevents achieving a good (MSE) fit over a relatively large range of photon energies.

To overcome the identified shortcommings in prior Oscillator Structure based Parametric Models for use in calculating Dielectric Function Component values, given a photon energy, and to meet the First Requirement recited in the Background Section, (ie. that a Dielectric Parametric Function Model provide sufficient flexibility to fit essentially any empirically derived data set). That is, Oscillator Structures should preferably allow sufficient degrees of freedom to allow "Peak" and "Tail" regions thereof to be mathematically modeled essentially independently. The preferred embodiment of such an Oscillator Structure provides that Finite Order Polynomials, (providing terms of any Order), and possibly Finite Magnitude Discontinuities, should be combined to form "Oscillator Structures". A typical 983 Patent Oscillator Structure is comprised of two Finite Order Polynomials (F1 and F2), to the left of a Center Point region, said two Finite Order Polynomials, (F1 and F2), being sequentially continuous in zero (0), first (1) and preferably second (2) derivatives at their point of merger; said two polynomials, (F1 and F2), being possibly followed by a Finite Magnitude Discontinuity; with the resulting foregoing described partial Oscillator Structure being followed by two additional Finite Order Polynomials, (F3 and F4), to the right of the Finite Magnitude Discontinuity, which Finite Order Polynomials, (F3 and F4), are sequentially continuous in zero (0), first (1) and preferably second (2) derivatives at their point of merger. It is also mentioned that a variation of a basic Oscillator Structure provides that some of the Finite Order Polynomials can be eliminated or made to contain only various Order Terms, (eg. that is contain any of zero, first, second, third etc. Order terms, and possibly not others), and still provide a functional Oscillator Structure. For instance, there might be only one Finite Order Polynomial on one or both sides of an Oscillator Structure Center Point, and a Finite Magnitude Discontinuity might, or might not, be present and might, or might not, be preceded or followed by a Finite Order Polynomial, for instance. In any case, each oscillator Structure, (assuming more than one such Oscillator Structure is utilized), begins and ends at dependent variable (e1) and/or (e2) values of zero (0), at an independent variable photon energy which is that corresponding to the Center Point of an Oscillator Structure, which can be that of the same, or another, Oscillator Structure. (Note if both the beginning and end of an Oscillator Structure are present at the Center Point of the same Oscillator Structure, a Zero-Width Finite Magnitude Oscillator Structure "Pole" results, which is mathematically equivalent to a Finite Magnitude Discontinuity which begins at zero of a dependent variable scale at the Center Energy of the independent variable. This equivalency allows various approches to computer programming implementation).

It is noted that Finite Order Polynomials and Finite Magntude Discontinuities are selected as components of Oscillator Structures because said mathematical entities can be subjected to a Convolution Integration, (a procedure involving, in the present case, the product of such a Finite Order Polynomial, with or without an associated Finite Magnitude Discontinuity; and a Broadening Factor, (preferrably Gaussian), which involves Error Functions and/or Exponentials, see supra). If only Finite Order Polynomials and Finite Magnitude Discontinuities are utilized to construct non-Zero-Width Oscillator Structures, analytic functions and published Integral Tables, (see the "Handbook of Mathematical Functions", Abromowitz and Stegun, Dover Publications, 1972 and "Table of Integrals, Series and Products", Gradshteyn and Ryzhik, Academic Press, 1980, which references are incorporated by reference herein), are available which allow relatively easy evaluation of required Oscillator Structure Model Convolution Integrals which arise from the application of an Oscillator Structure "Broadening Factor".

As regards application in the presently disclosed invention, it is important to realize that use of 983 Oscillator Structures can be difficult in conventional fitting precedures which require appropriate positioning of Oscillator Structures. The present invention overcomes this difficulty by simply defining segments in an (e2) plot, and mechanically assigning an oscillator which has definite beginning and end points structure in each.

Conventional practice typically involves inspection of Dielectric Function (e2) vs. photon energy to determine the location(s) at which "Dependent Variable Peaks" exist. Use of plotted Dependent vs. Independent Variable data is useful in performing this inspection. The independent variable "Center Point" of an oscillator Structure is then located at the photon energy corresponding to each Peak, with Polynomial Modeled Tails projecting to one or both sides thereof. An Oscillator Structure Finite Magnitude Discontinuity might also be positioned at a Center Point. (In the case where a Dependent Variable Peak corresponds to the Band-Gap Edge in a Semiconductor, Dielectric Function Component Magnitudes often demonstrate essentially Discontinuous "Jumps" over very small changes in Energy, at a photon energy corresponding to the edge of said Band-Gap. The inclusion of Finite Magnitude Discontinuities in the Model speaks to Sixth (6) Requirement recited in the Background Section of this Disclosure in which it is stated that a Model might provide physically relevant parameters therein, eg. a Bandgap absorption edge). Also, each Finite Width Oscillator Structure so positioned will begin and end at an independent variable (e2) value of zero (0), which zero (0) values are, (assuming more than one Oscillator Structure is present), located at the Center Point Energy of a positioned Oscillator Structure, which, as alluded to above, can be the same or another Oscillator Structure. This approach to locating the beginnings and ends of Oscillator Structures positioned on a plot of (e2) vs. photon energy, at the Center Point Energy of other Oscillator Structures, allows moving a Center Point Energy position in relation to other Center Point Energy positions without causing drastic effects in Model produced results at distal photon energies. This approach to locating lower and upper energy end-points of Oscillator Structures is absolutely essential to application of the present invention.

With an "appropriately" estimated number of appropriately constructed Oscillator Structure(s) positioned along a photon energy axis of an (e2) vs. photon energy plot, a Finite Order Polynomial Coefficient and Finite Magnitude Discontinuity Magnitude defining Oscillator Structure Mathematical Model Parameter evaluation routine, including applied Broadening Factors, can be applied to simultaneously provide values for all Oscillator Structure Mathematical Model Coefficients, based upon, for instance, a Mean-Square-Error (MSE) criteria. (A typical Coefficient evaluation routine might utilize a Levenberg-Marquard approach). Use of said Finite Order Polynomial Coefficients and Finite Discontinuity Magnitudes in constructing Oscillator Structures then allows evaluation of Oscillator Structure Mathematical Model Coefficients, in view of Convolution Integration applied Broadening Factors, which Mathematical Model Coefficients are utilized in evaluation of dependent variable, such as (e2) values, provided an independent variable value, such as photon energy. It will be appreciated that Oscillator Structure Mathematical Model Coefficient values for each Oscillator Structure utilized are all that have to then be available to allow calculation of a value of, for instance, (e2), given a value of, for instance, photon energy, when required. If, for example, the number of Oscillator Structures utilized is seven (7), and twelve (12) variables are found necessary to define each, then only eighty-four (84) Coefficient values must be stored. Thereafter, when a value of dependent variable (e2) for a given independent variable photon Energy level (ES) is desired, the various Finite Order Polynomials which are present in a range of photon energies in which the specific photon energy (ES) of interest is present are produced and evaluated at said photon energy (ES) value of interest, and the contributions of each Finite Order Polynomial are added together by a summation procedure. If necessary the value of a Finite Magnitude Discontinuity, (be it additive or subtractive), is included in the summation.

Now, in use, one can try a number of "Mathematical Models". That is, it might be found that while seven (7) Oscillator Structures, each providing four (4) Polynomials, each of second (2) order, provide a good (MSE) fit over the range of Energies involved, some of the attendant Coefficients of the Mathematical Model for oscillator Structures are strongly "Correlated", such that change in one thereof is attended by a directly off-setting change in one or more of the others. That would be indicative of (e2) vs. photon energy Data which are not "strong" enough to justify the number of Coefficients requiring evaluation assumed into the Mathematical Model. One might then try eliminating one or more present Oscillator Structures or possibly one or more Finite Order Polynomials from one or more of the Oscillator Structures, or perhaps one might try reducing the number of Polynomial Order Terms in one or more Finite Order Polynomials present, and rerunning the Mathematical Model Coefficient evaluating program. If an equally good (MSE) fit is obtained, and less Mathematical Model Coefficient Correlation is present, the "Modified Mathematical Model" would be considered superior in a conventional sense. In use it has been found that far less than the above mentioned eighty-four (84) parameters are required to adequately characterize, for instance, the (e2) vs. photon energy Function of a Gallium-Arsonide Sample System. (Note, a highly corelated model is capable of providing equally as accurate Dielectric Function values as a non-correlated model. Correlation problems, however, are troublesome when arriving at the model, and when, for instance, attempting to apply it to alloy materials etc.)

As regards application in the presently disclosed invention, it is important to realize that use of 983 Oscillator Structures can be difficult in conventional fitting precedures which require appropriate positioning of Oscillator Structures. The present invention overcomes this difficulty by simply defining segments in an (e2) plot, and mechanically assigning an oscillator which has definite beginning and end points structure in each.

Oscillator Structures are best described graphically. With this in mind it should be appreciated that the present invention will be better understood by reference to the Detailed Description Section, in coordination with the accompanying Drawings.

DETAILED DESCRIPTION

It is announced at this point that FIGS. 1–4e and 5 and 6 are incorporated from U.S. Pat. No. 5,796,983 for general insight, FIGS. 4f–4k identify additional oscillator structures which can be applied in present invention, and FIGS. 7–8k demonstrate the presently disclosed invention methodology.

Figure 1:
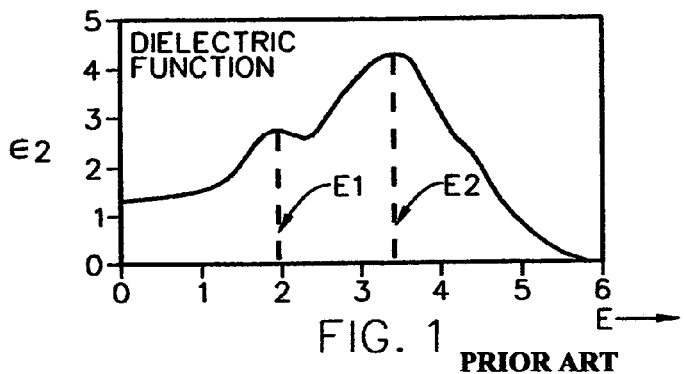
FIG. 1 shows a plot of the imaginary component of an assumed Dielectric Function vs. Energy level, presenting with two Peak Regions.
Figure 2:
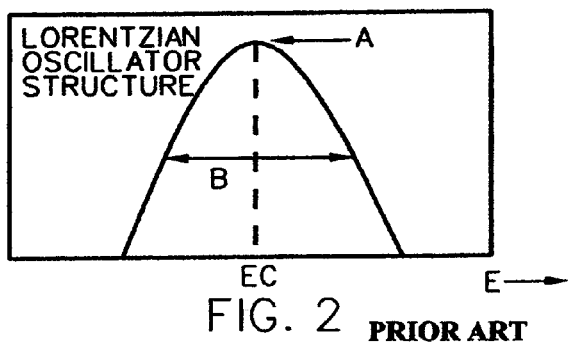
FIG. 2 shows a basic Narrow Lorentzian Oscillator Structure in which the tail regions are negligible.
Figure 3:
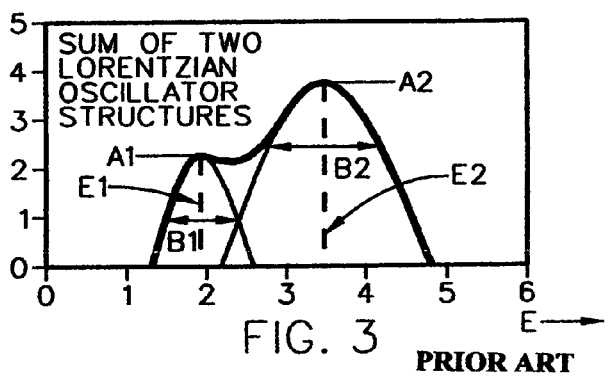
FIG. 3 shows the plot of FIG. 1, with two Narow Lorentzian Oscillator Structures applied thereto at the Peak Regions.

As disclosed in U.S. Pat. No. 5,796,983 and included herein for background and insight, there is shown in FIG. 1, a plot of data corresponding to the Imaginary Component (e2) of a presumed Dielectric Function vs. Energy, which plot is representative of that which might be obtained from investigation of a semiconductor material. Note the presence of two dependent variable "Peak" regions, located at "E1" and "E2" on the independent variable "X" axis. Next, FIG. 2 shows the general shape of a Narrow Lorentzian or Gaussian Oscillator Structure centered about a point labeled "EC" on the independent variable "X" axis. (While not shown other Mathematical "Oscillator Structures" could also be utilized for the purposes of this demonstration). Note that the Narrow Lorentzian or Gaussian Oscillator Structure in FIG. 2 presents with a Maximum dependent variable Magnitude "A" and is shown with a "Full-Width-Half-Maximum" (FWHM) Broadening "B", (which Broadening can extend from Zero (O) to, theoretically, any finite value). FIG. 3 shows two such Narrow Lorentzian or Gaussian Oscillator Structures positioned on the (e2) vs. photon energy plot of FIG. 1. One said Narrow Lorentzian or Gaussian Oscillator Structure is shown with a Maximum Magnitude of "A1", a (FWHM) Broadening of "B1", and it is centered about a point on the independent variable "X" axis labeled "E1". The second Narow Lorentzian Oscillator or Gaussian Structure is shown with a Maximum Magnitude of "A2", a (FWHM) Broadening of "B2", and it is centered about a point on the independent variable "X" axis labeled "E2". Note that the independent varaible "X" axis points "E1" and "E2" in FIG. 1 and FIG. 2 plots correspond to one another. FIG. 3 also provides, in bold, a line representing the summation of the contributions from the two present Narrow Lorentzian or Gaussian Oscillator Structures, at each energy, which bold line very roughly corresponds to the (e2) vs. photon energy plot in FIG. 1. Note that the plot in FIG. 1 is, however, very different from the bold line plot in FIG. 3, particularly in the "Tail" regions beyond each "Peak" region. This demonstrates the shortcommings of an attempt to use Lorentzian and Gaussian etc. Oscillator Structures to model the Imaginary Component (e2) of a Dielectric Function vs. Photon Energy. The Three (3) degrees of freedom, (ie. Maximum Magnitude, Broadening and Center Energy), which define each Lorentzian or Gausian Oscillator Structure, are simply typically not sufficient to allow achieving a "good" Model fit in both Peak and Tail regions of most (e2) vs. Energy plots. However, note that sufficient data is contained in six (6) Lorentzian Oscillator Structure defining parameters to provide a rough approximation to the (e2) vs. Energy data. This compares with hundreds, or even thousands of data points were the plot in FIG. 1 is determined and characterized as a table of data. Of course, additional Lorentzian Oscillator Structures could be added to the plot in FIG. 3, in an attempt to improve the approximation result, but this approach has not been found capable of providing results sufficient for use in Ellipsometer System settings, emphasis added.

Figure 4A:
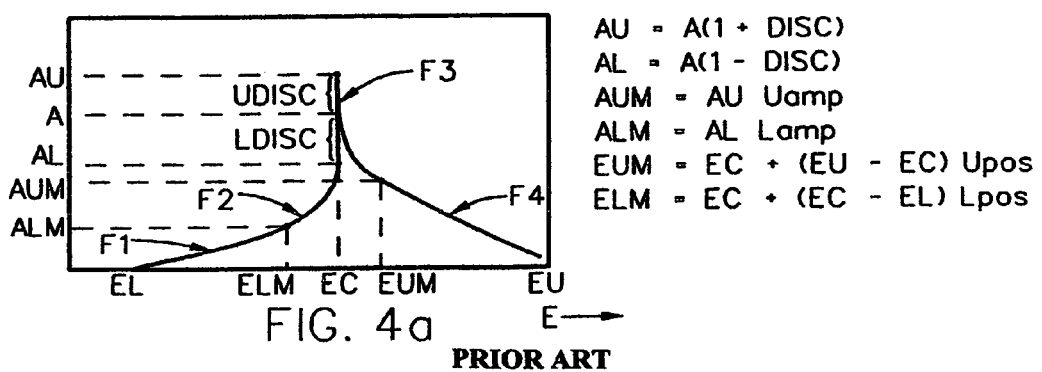
FIGS. 4a–4d show various Oscillator Structures constructed by various application of Finite Order Polynomials and Discontinuities.
Figure 4B:
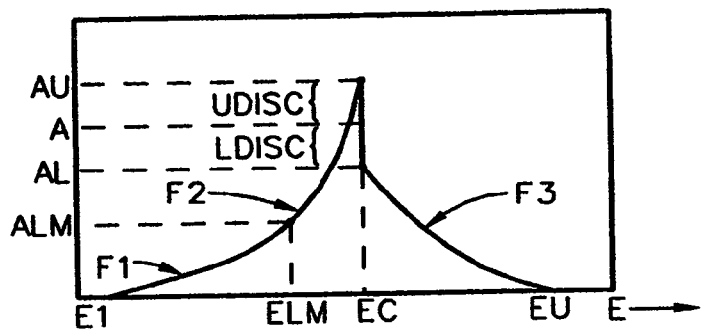
Figure 4C:
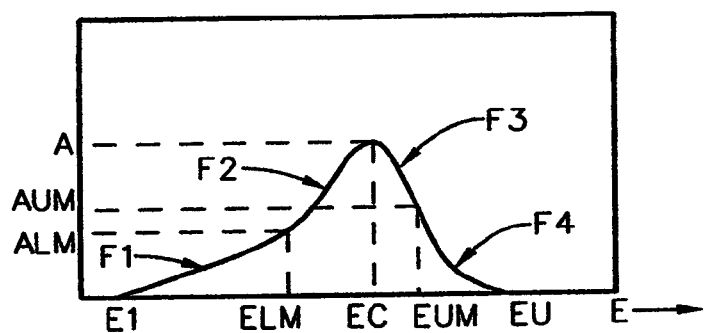
Figure 4D:
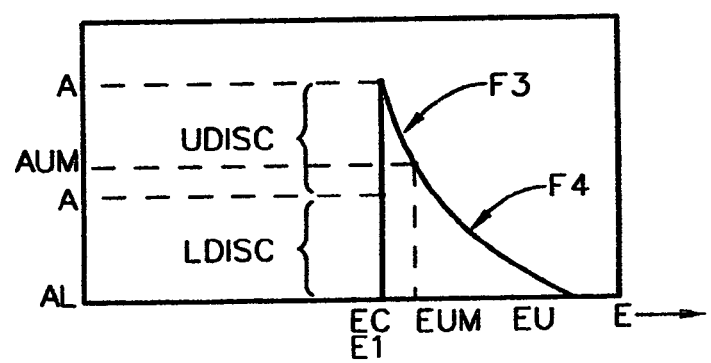
Figure 4E:
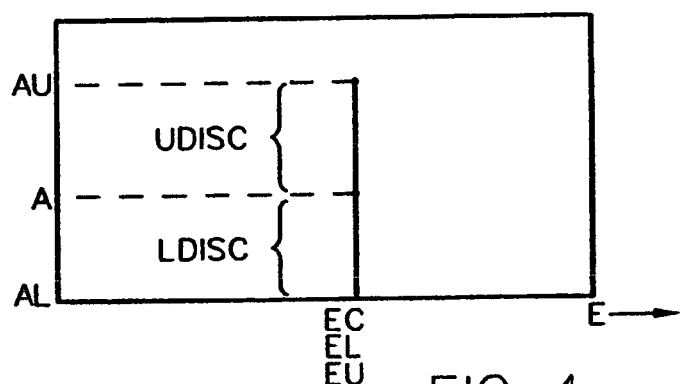
FIG. 4e shows a Zero-Width Oscillator Structure, (ie. a Pole), constructed by application of coincident Lower, Center and Upper Energy levels and an Amplitude, or alternatively, a Discontinuity at a Center Energy level.
Figure 4F:
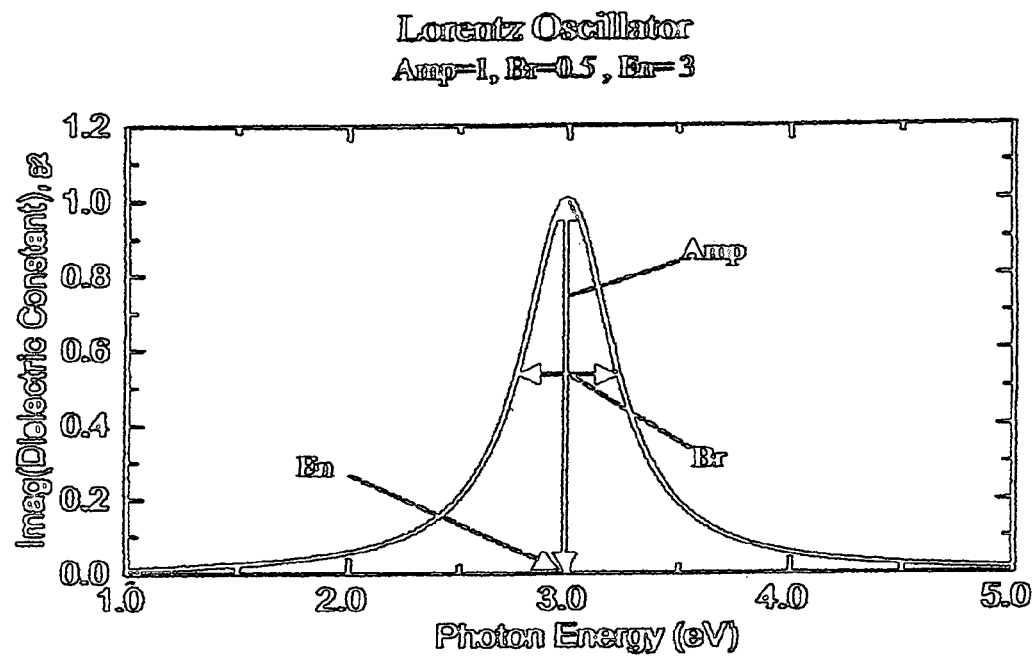
FIGS. 4f and 4g show Lorentz and Gaussian Oscillators.
Figure 4G:
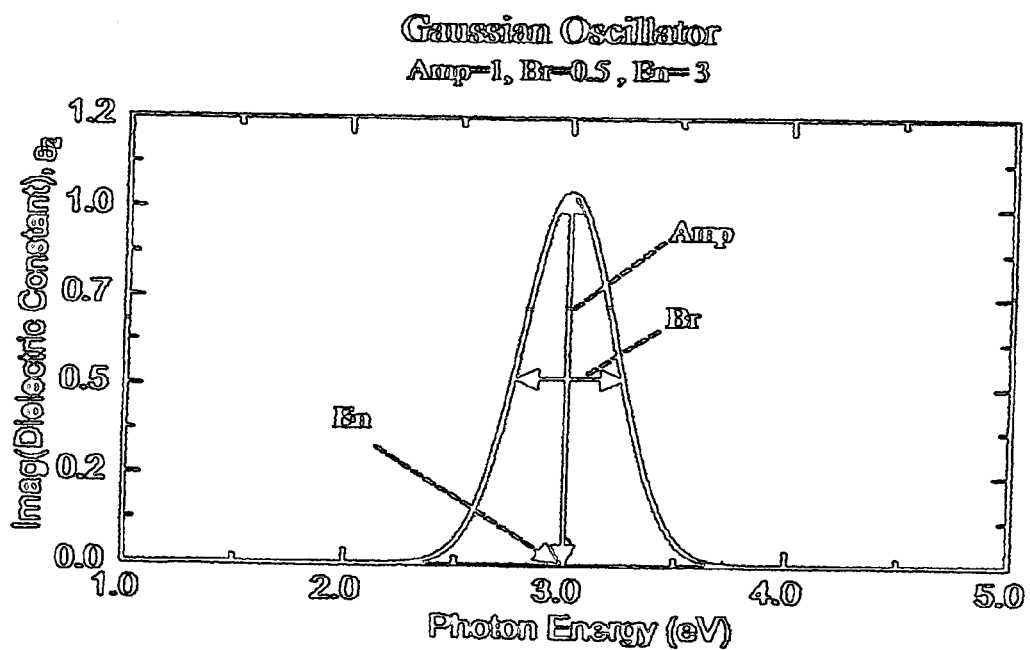
Figure 4H:
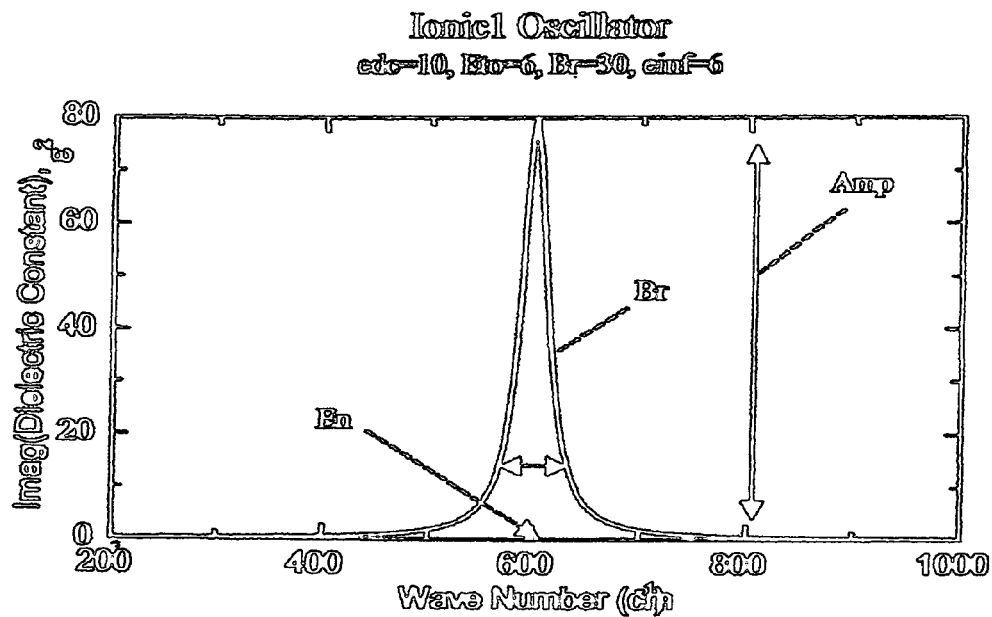
FIGS. 4h, 4i, 4j and 4k respectively show Ionic1, Ionic2, Harmonic, TOLO, and the like Oscillator Structures.
Figure 4I:
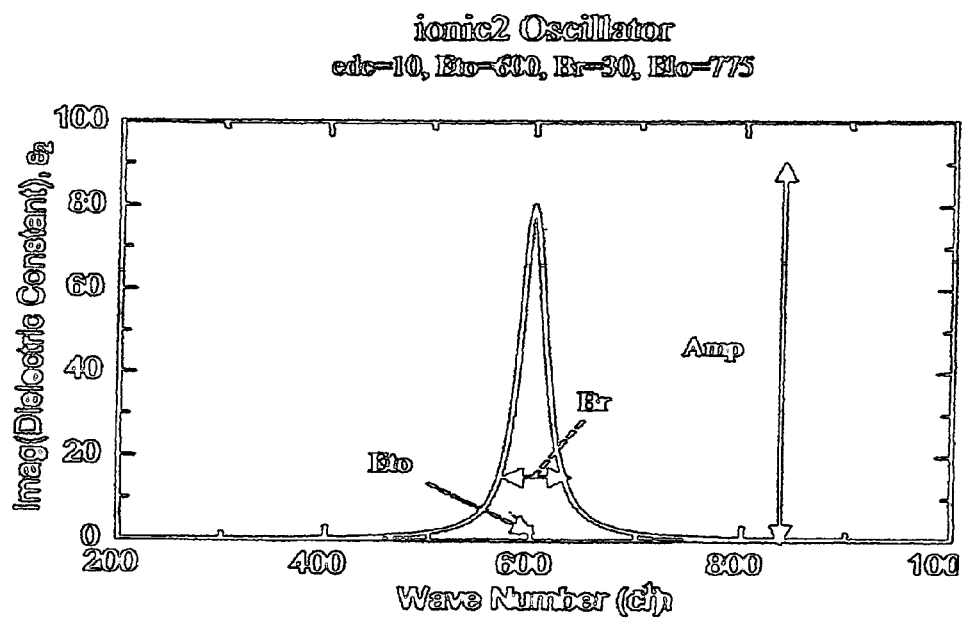
Figure 4J:
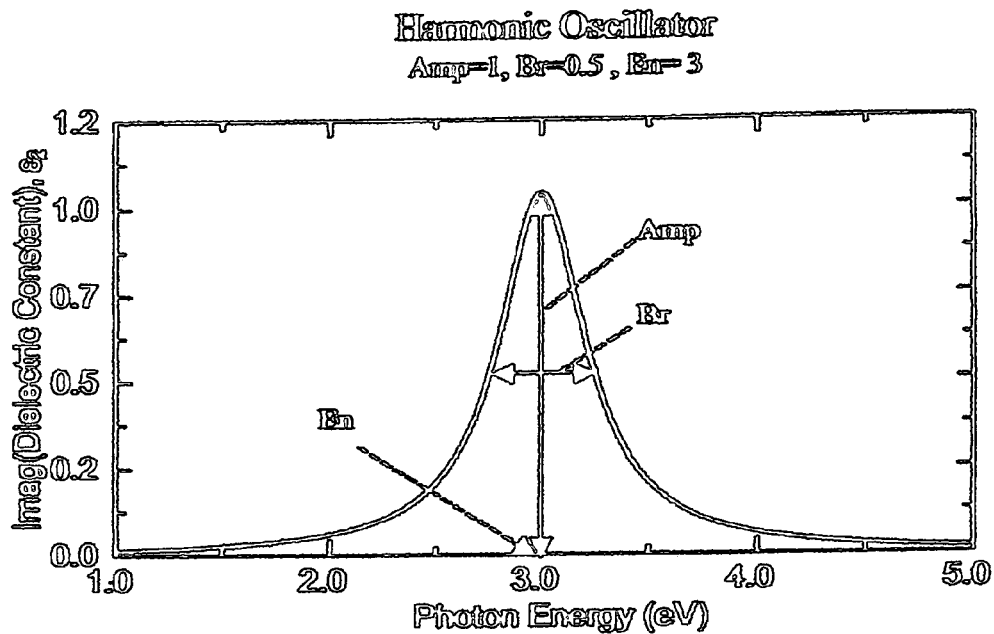

Note that FIGS. 4f and 4g show Lorentz and Gaussian Oscillators in better detail. Shown are Central Energies (En), Amplitude (Amp) and Broadening (Br). It is to be appreciated that where the Broadening (Br) is small in the Lorentz FIG. 4f Oscillator, the Tail Regions quickly decay to an effective intersection with the horizontal axis, as demonstrated in FIGS. 2 and 3. Note, variations on the Lorentz and Gaussian Oscillators include Ionic1, Ionic2, Harmonic, TOLO Structures as indicated in FIGS. 4h, 4i, 4j and 4k respectively. Said additional Oscillator Structures are described in the J.A Woollam Co. WVASE Manual, which is incorporated by reference herein. Equations presented In the J.A. Woollam CO. WVASE Manual are included directly to provide insight to the Form of the Mathematical Equations which define them:

| Style | Equation | Fit Parameters |
|---|---|---|
| | Gaussian: | |
| | $\varepsilon_{n\_Gaussian} = \varepsilon_{n1} + i\varepsilon_{n2}$, where $\varepsilon_{n1} = \frac{2}{\pi} P \int_0^\infty \frac{\xi \varepsilon_{n2}(\xi)}{\xi^2 - E^2} d\xi$, | |
| | using $\epsilon_{n2}$ as defined below. | |
| Gau.0 (eV) | $\varepsilon_{n2} = A_n e^{-\left(\frac{E-E_n}{Br_n}\right)^2} + A_n e^{-\left(\frac{E+E_n}{Br_n}\right)^2}$ | Ampn = $A_n$ (dimensionless), Enn = $E_n$ (eV), Brn = $Br_n$ (eV) |
| Gau.5 (cm$^{-1}$) | | Ampn = $A_n$ (dimensionless), En1 = $E_n$ (cm$^{-1}$), Br1 = $Br_n$ (cm$^{-1}$) |

-continued

| Style | Equation | Fit Parameters |
|---|---|---|
| Gau.1 (eV) | $\varepsilon_{n2} = \dfrac{A_n}{Br_n} e^{-\left(\frac{E-E_n}{Br_n}\right)^2} + \dfrac{A_n}{Br_n} e^{-\left(\frac{E+E_n}{Br_n}\right)^2}$ | Ampn = $A_n$ (eV), Enn = $E_n$ (eV), Brn = $Br_n$ (eV) |
| Gau.6 (cm$^{-1}$) | | Ampn = $A_n$ (cm$^{-1}$), Enn = $E_n$ (cm$^{-1}$), Brn = $Br_n$ (cm$^{-1}$) |
| Gau.2 (eV) | $\varepsilon_{n2} = \dfrac{A_n E_n}{Br_n} e^{-\left(\frac{E-E_n}{Br_n}\right)^2} + \dfrac{A_n E_n}{Br_n} e^{-\left(\frac{E+E_n}{Br_n}\right)^2}$ | Ampn = $A_n$ (dimensionless), Enn = $E_n$ (eV), Brn = $Br_n$ (eV) |
| Gau.7 (cm$^{-1}$) | | Ampn = $A_n$ (dimensionless), Enn = $E_n$ (cm$^{-1}$), Brn = $Br_n$ (cm$^{-1}$) |
| | <u>Lorentz</u> | |
| Lor.0 (eV) | $\varepsilon_{n\_Lorentz} = \dfrac{A_n Br_n E_n}{E_n^2 - E^2 - i Br_n E}$ | Ampn = $A_n$ (dimensionless), Enn = $E_n$ (eV), Brn = $Br_n$ (eV) |
| Lor.5 (cm$^{-1}$) | | Ampn = $A_n$ (dimensionless), En1 = $E_n$ (cm$^{-1}$), Br1 = $Br_n$ (cm$^{-1}$) |
| Lor.1 (eV) | $\varepsilon_{n\_Lorentz} = \dfrac{A_n E_n}{E_n^2 - E^2 - i Br_n E}$ | Ampn = $A_n$ (eV), Enn = $E_n$ (eV), Brn = $Br_n$ (eV) |
| Lor.6 (cm$^{-1}$) | | Ampn = $A_n$ (cm$^{-1}$), Enn = $E_n$ (cm$^{-1}$), Brn = $Br_n$ (cm$^{-1}$) |
| Lor.2 (eV) | $\varepsilon_{n\_Lorentz} = \dfrac{A_n E_n^2}{E_n^2 - E^2 - i Br_n E}$ | Ampn = $A_n$ (dimensionless), Enn = $E_n$ (eV), Brn = $Br_n$ (eV) |
| Lor.7 (cm$^{-1}$) | | Ampn = $A_n$ (dimensionless), Enn = $E_n$ (cm$^{-1}$), Brn = $Br_n$ (cm$^{-1}$) |
| | <u>Harmonic:</u> | |
| Lor.0 (eV) | $\varepsilon_{n\_Harmonic} = \dfrac{A_n Br_n E_n}{E_n^2 - E^2 + 1/4 Br_n^2 - i Br_n E}$ | Ampn = $A_n$ (dimensionless), Enn = $E_n$ (eV), Brn = $Br_n$ (eV) |
| Lor.5 (cm$^{-1}$) | | Ampn = $A_n$ (dimensionless), En1 = $E_n$ (cm$^{-1}$), Br1 = $Br_n$ (cm$^{-1}$) |
| Lor.1 (eV) | $\varepsilon_{n\_Harmonic} = \dfrac{A_n E_n}{E_n^2 - E^2 + 1/4 Br_n^2 - i Br_n E}$ | Ampn = $A_n$ (eV), Enn = $E_n$ (eV), Brn = $Br_n$ (eV) |
| Lor.6 (cm$^{-1}$) | | Ampn = $A_n$ (cm$^{-1}$), Enn = $E_n$ (cm$^{-1}$), Brn = $Br_n$ (cm$^{-1}$) |
| Lor.2 (eV) | $\varepsilon_{n\_Harmonic} = \dfrac{A_n E_n^2}{E_n^2 - E^2 + 1/4 Br_n^2 - i Br_n E}$ | Ampn = $A_n$ (dimensionless), Enn = $E_n$ (eV), Brn = $Br_n$ (eV) |
| Lor.7 (cm$^{-1}$) | | Ampn = $A_n$ (dimensionless), Enn = $E_n$ (cm$^{-1}$), Brn = $Br_n$ (cm$^{-1}$) |
| | <u>Ionic1 & Ionic2:</u> | |
| Ion1.0 (eV) | $\varepsilon_{n\_Ion1} = \varepsilon_{dcn} + \dfrac{E_{Tn}^2 (\varepsilon_{dcn} - \varepsilon_{in})}{E_{Tn}^2 - E^2 - i Br_n E}$ | edcn = $\epsilon_{dcn}$ (dimensionless), einfn = $\epsilon_{an}$ (dimensionless), Eion = $E_{Tn}$ (eV), Brn = $Br_n$ (eV) |
| Ion1.5 (cm$^{-1}$) | | edcn = $\epsilon_{dcn}$ (dimensionless), einfn = $\epsilon_{an}$ (dimensionless), Eion = $E_{Tn}$ (cm$^{-1}$), Brn = $Br_n$ (cm$^{-1}$) |
| Ion2.0 (eV) | $\varepsilon_{n\_Ion1} = \varepsilon_{dcn} \left( \dfrac{E_{Tn}^2}{E_{Ln}^2} + \dfrac{E_{Tn}^2 \left(1 - \dfrac{E_{Tn}^2}{E_{Ln}^2}\right)}{E_{Tn}^2 - E^2 - i Br_n E} \right)$ | edcn = $\epsilon_{dcn}$ (dimensionless), Eion = $E_{Tn}$ (eV), Brn = $Br_n$ (eV), Eion = $E_{Ln}$ (eV) |
| Ion2.5 (cm$^{-1}$) | | edcn = $\epsilon_{dcn}$ (dimensionless), Eion = $E_{Tn}$ (cm$^{-1}$), Brn = $Br_n$ (cm$^{-1}$), Eion = $E_{Ln}$ (eV) |

-continued

| Style | Equation | Fit Parameters |
|---|---|---|
| TOLO: | | |
| TOLO.0 (eV) | $\varepsilon_{n\_TOLO} = A_n \dfrac{E_{ton}^2 - E^2 - iB_{ion}E}{E_{ton}^2 - E^2 - iB_{ion}E}$ | Ampn = $A_n$ (dimensionless), Eion = $E_{ion}$ (eV), $E_{ion}$ = Eion (eV) Bion = $B_{ion}$ (eV), Bion = $B_{ion}$ (eV) |
| TOLO.5 (cm$^{-1}$) | | Ampn = $A_n$ (dimensionless), Eion = $E_{ion}$ (cm$^{-1}$), $E_{ion}$ = Eion (cm$^{-1}$) Bion = $B_{ion}$ (cm$^{-1}$), Bion = $B_{ion}$ (cm$^{-1}$) |
| TOLO.1 (eV) | $\varepsilon_{n\_TOLO} = \dfrac{A_n E_{ton}^2 - E^2 - iB_{ion}E}{B_{ion}E_{ton}^2 - E^2 - iB_{ionn}E}$ | Ampn = $A_n$ (eV), Eion = $E_{ion}$ (eV), $E_{ion}$ = Eion (eV) Bion = $B_{ion}$ (eV), Bion = $B_{ion}$ (eV) |
| TOLO.6 (cm$^{-1}$) | | Ampn = $A_n$ (cm$^{-1}$), Eion = $E_{ion}$ (eV), $E_{ion}$ = Eion (eV) Bion = $B_{ion}$ (eV), Bion = $B_{ion}$ (eV) |
| TOLO.2 (eV) | $\varepsilon_{n\_TOLO} = A_n \dfrac{E_{ion}E_{ton}^2 - E^2 - iB_{ion}E}{B_{ion}E_{ton}^2 - E^2 - iB_{ion}E}$ | Ampn = $A_n$ (dimensionless), Eion = $E_{ion}$ (eV), $E_{ion}$ = Eion (eV) Bion = $B_{ion}$ (eV), Bion = $B_{ion}$ (eV) |
| TOLO.7 (cm$^{-1}$) | | Ampn = $A_n$ (dimensionless), Eion = $E_{ion}$ (cm$^{-1}$), $E_{ion}$ = Eion (cm$^{-1}$) Bion = $B_{ion}$ (cm$^{-1}$), Bion = $B_{ion}$ (cm$^{-1}$) |

It is to be appreciated that for application in the presently disclosed invention, the functional requirement is that an Oscillator must provide substantially definite starting and ending intersection points with the horizontal axis so that an end point of one Oscillator can be vertically aligned with peak point of an adjacent Oscillator. The 983 Patent Oscillator Structure which is reviewed herein in detail, is preferred as it can be constructed to meet said functional requirment as demonstrated well in FIGS. 4a–4c.

The forgoing then, demonstrates the concept of utilizing a summation of contributions from a plurality of Mathematical Structures to attempt to Model a plot of, for instance, (e2) vs. Energy data, in a manner which requires determination of a reduced number of parameter values, (as compared to an approach utilizing, for instance, tabulated data), and the foregoing also identifies the shortcommings of the demonstrated approach. The preferred realization of the present invention serves to overcome the identified shortcommings by utilizing novel Oscillator Structures which provide more available degrees of freedom than provided by, for instance, the Lorentzian Oscillator Structure. This is accomplished by utilization of defined novel Oscillator Structure(s), which allow shaping the "Peak" and "Tail" regions thereof, (which "Tail" Regions project to the right and left of a "Peak" Region Center Point thereof), in a very non-correlated manner. The use of a "Broadening Factor" applied over the full range of an Oscillator Structure, conceptually similar to that described infra with respect to the Lorentzian Oscillator Structure, is retained, but application thereof to a present invention Oscillator Structure is accomplished via Mathematical Convolution Integrations applied simultaneously, but independently, to various regions of an Oscillator Structure. This is required, because as described directly herein, different independent variable regions of an Oscillator Structure are defined, for instance, by contributions from different Finite Order Polynomials and/or Discontinuities.

Turning now to FIG. 4a, there is shown a general representation of a novel Oscillator Structure disclosed in U.S. Pat. No. 5,796,983. Note that Four (4) Finite Order Polynomial defined regions, and one Finite Magnitude Discontinuity are shown. The Four (4) defining Polynomials are identified as F1, F2, F3 and F4, with F1 beginning at coordinates (0,EL), and merging with Polynomial F2 at coordinate (ALM,ELM). Polynomial F2 is terminated at coordinate (AL,EC) by the lower end of the LDISC region of the Discontinuity, (shown as two dimensionless regions, labeled UDISC and LDISC, above and below coordinates (A,EC)) respectively. (Note that the magnitudes of UDISC and LDISC are typically selected to be of equal finite Dimensionless Magnitudes). The upper end of the UDISC region ends at coordinates (AU,EC), whereat Polynomial F3 begins. Polynomial F3 extends to a merger with Polynomial F4 at coordinates (AUM,EUM), and Polynomial F4 intersects the independent variable "X" axis at coordinate (0,EU).

As required Oscillator Structure defining Mathematical Model Coefficients for the above described Oscillator Structure(s), the following, underlined, Nine (9) Coefficients were chosen in the 983 Patent disclosure for evaluation and application in the practice of the Method of use described therein:

A;

EL;

EC;

EU;

AU=A*(1+UDISC);

AL=A*(1−LDISC); (Note UDISC and LDISC are of equal magnitude)

AUM=AU*Uamp;

ALM=AL*Lamp;

EUM=EC+(EU−EC)*Upos;

ELM=EC−(EC−EL)*Lpos.

In addition, a Broadening Factor, Sigma (σ), assumed to be, but not necessarily, Gaussian, is also evaluated to determine a defined Oscillator Structure. (Note, Gaussian Broadening is preferred because convenient, and novely applied, Mathematical aides are available when such is the case, as described elsewhere in this Disclosure. It is to be understood that other Broadening criteria can be utilized and remain within the scope of the present invention.)

The "Order" of the various Finite Order Polynomials must also be identified, and such is accomplished with the use of two (2) additional parameters as follows:

For EL<E<ELM:

$$F1 = ALM*((1-L2d)*y1 + L2d*y1^2)$$

For ELM<E<EC $$F2 = (ALM + (1-ALM)*(1-cl-dl)*y2 + cl*y2^2 + dl*y2^4))$$

For EC<E<EUM $$F3 = (AUM + (1-AUM)*(1-cu-du)*y4 + cu*y4^2 + du*y4^4))$$

For EUM<E<EU $$F4 = AUM*((1-U2d)*y3 + U2d*y3^2)$$

where:

$$cl = L2d*(ALM/(1-ALM))*((EC-ELM)/(ELM-EL))^2$$

$$dl = ((1/(1-ALM))*(1-((EC-ELM)/(ELM-EL))*ALM*(EC-EL)*((L2d/(ELM-EL)) + (1/(EC-ELM)))$$

$$cu = U2d*(AUM/(1-AUM))*((EC-EUM)/(EUM-EU))^2$$

$$du = ((1/(1-AUM))*(1-((EC-EUM)/(EUM-EU))*AUM*(EC-EU)*((U2d/(EUM-EU)) + (1/(EC-EUM)))$$

and where:

$$y1 = (E-EL)/((ELM-EL);$$

$$y2 = (E-ELM)/(EC-ELM);$$

$$y3 = (EU-E)/(EU-EUM);\ \text{and}$$

$$y4 = (EUM-E)/(EUM-EC);$$

(Note that the y1 and y2 as used here are not the same as the y1 and y2 as defined with respect to EQ. 3 in the Disclosure of the Invention Section herein. The y1 and y2 in the disclosure of the Invention Section are related to a Gaussian Broadening Factor).

are normalized energy terms. The significance of the use of "normalized" energy terms is particularly critical in application where Gaussian Broadening of Oscillator Structures is utilized. Briefly, use of normalized energy terms allows Convolution integration of a product of a Finite Order Polynomial and a Gaussiam Broadening Factor to provide one-dimensional, normalized, independent variable based Look-up Tables to allow convenient evaluation of corresponding dependent variables. Said significance is described more fully in the Disclosure of the Invention Section herein.

FIG. 4b shows another Oscillator Structure formed from the same basic components as that in FIG. 4a, (eg. Finite Order Polynomials and Finite Magnitude Discontinuities), but in which Polynomial F2 and the upper end of UDISC meet at coordinates (AU,EC) and Polynomial F3 begins at coordinates (AL,EC) and ends at coordinates (0,EU). Note that no Polynomial F4 is present. This is demonstrative of the fact that some or all of the Four Polynomials shown in FIG. 4a can be absent while still defining an Oscillator Structure. In that light note that FIG. 4e shows the case where no F1–F4 Polynomials are present, with the result being a "Zero-Width-Finite-Magnitude Oscillator Structure", or "Pole", of Zero-Width, (ie. (EL), (EC) and (EU) are coincident), but with a Finite Magnitude (AU) above the independent variable "X" coordinate (EC). (Note that FIG. 4e can alternatively be considered to show a Discontinuity of Finite Magnitude (AU) above the dependent variable zero (0) level, present at photon energy (EC), said Finite Magnitude Zero-Width Oscillator and Finite Magnitude Discontinuity interpretations being equivalent mathematically). FIG. 4c shows a case wherein Polynomials F1, F2, F3 and F4 are present, but no Discontinuity DISC, (ie. UDISC and LDISC, which are of equal Finite Magnitude), is present. Polynomials F2 and F3 merge at coordinates (A,EC), which correspond to a "Peak" in this Figure. FIG. 4d shows a case in which a Discontinuity is present at "X" axis coordinate (EC), and in which Polynomials F3 and F4 are present, but Polynomials F1 and F2 are absent. It is to be understood that an analogous case wherein a Finite Magnitude Discontinuity and Finite Order Polynomials F1 and F2 are present to the left thereof, but where Finite Order Polynomials F3 and F4 are absent can also be constructued and such consitutes an Oscilator Structure. It should also be appreciated that a single Finite Order Polynomial with comprising Terms thereof of opposite signs can serve to provide a peaked Dependent Variable vs. Independent Variable Plot, which begins at an dependent Variable value of zero (0.0), and returns to a dependent Variable value of zero (0.0) at some Dependent Variable value. For instance the Finite Order Polynomial (Y=3*X-X^2) begins at a "Y" value of zero (0.0) at "X"=(0.0) and returns to a "Y"=(0.0) at "X"=(3.0). Such a Single Finite Order Polynomial can serve as an additional Oscillator Structure, (over a range of (0.0) to (3.0)), although coordination with other Oscillator Structures and application of Convolution Integral effected Broadening thereto, presents difficulties.

It is to be noted that where two Polynomials merge, (eg. F1 and F2, F3 and F4, or, possibly, when present without a Finite Magnitude Zero-Width Discontinuity therebetween, F2 and F3), they do so with continuous zero, first and preferably second (2) derivatives at the point of their merger. This is handled by the Mathematical Model Coefficient evaluation programming involved in implementing the invention.

Figure 8A:
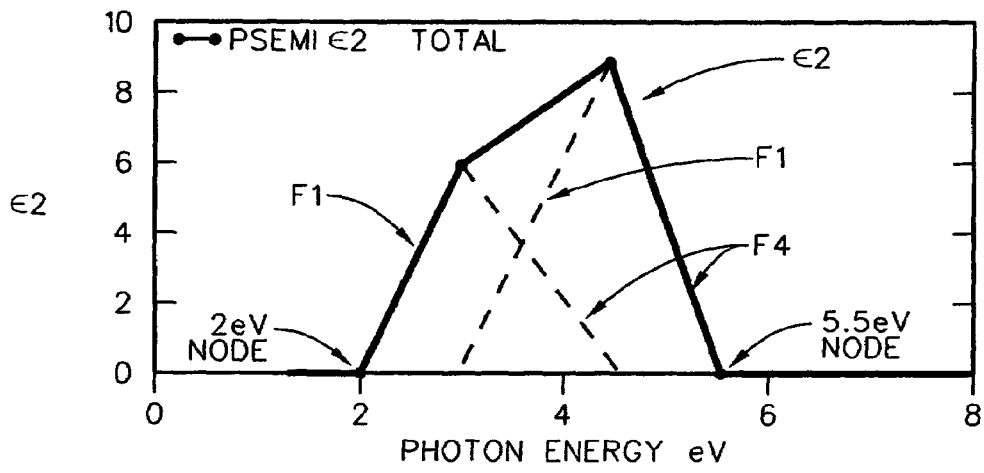
FIGS. 8a–8j demonstrate steps in the presently disclosed method of fitting Oscillator Structures to the imaginary part (e2) of a sample Dielectric Function.
Figure 8B:
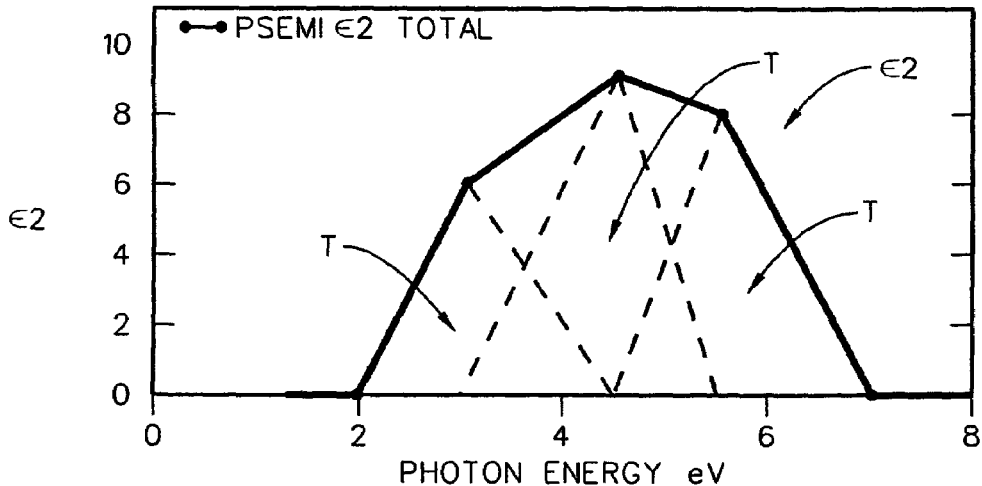

It is also noted that the straight line components of the Oscillator Structure shown in FIGS. 4a–4e can be combined to form Triangular (T) Oscillator Structures as demonstrated in FIGS. 8a and 8b, and shown applied in FIGS. 8c–8k. Said Triangular (T) shaped Oscillator Structures are a preferred, though not exclusive, structure in practice of the present invention methodology.

It should then be appreciated that the Oscillator Structures just described be constructed from one or more Finite Order Polynomial(s) and Finite Magnitude Discontinuities in various sequences, and that in the presently preferred embodiment, a typical, non-limiting Oscillator Structure can include from zero (0) to Four (4), Finite Order Polynomials, each present Finite Order Polynomial including terms of any Finite Order, (eg. zero and/or first and/or second and/or third etc.), and being positioned to the right or to the left of a Center Point; and that Oscillator Structures can include Finite Magnitude Discontinuities therein, present at Center Points thereof. It is also to be understood that acceptable such Oscillators include those of Zero (0) width, (ie. Poles) in which no Polynomials are present, said Poles being mathematically equivalent to a single Zero-Width Finite Magnitude Discontinuity, beginning at a dependent variable value of zero and positioned at a specified independent location.

In conventional useage, various constructed Oscillator Structures are positioned, by a user, at appropriate locations in regions along an independent variable "X" axis, which locations correspond to "Peak" locations regions in a plot of, for instance, the dependent variable Imaginary Component of a Dielectric Function (e2) vs. Photon Energy, and via Mathematical Convolution Integration, appropriate constructed Oscillator Structures are subjected to Gaussian Broadening.

Figure 5:
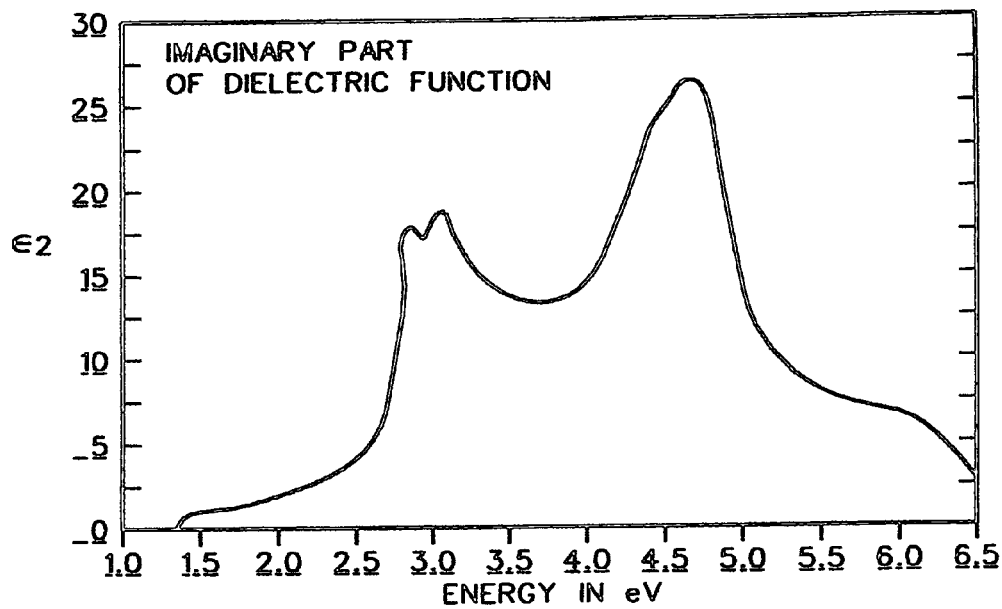
FIG. 5 shows a plot of an actual Imaginary Component of a Dielectric Function vs. Energy level for a Gallium-Arsonide Sample System.
Figure 6:
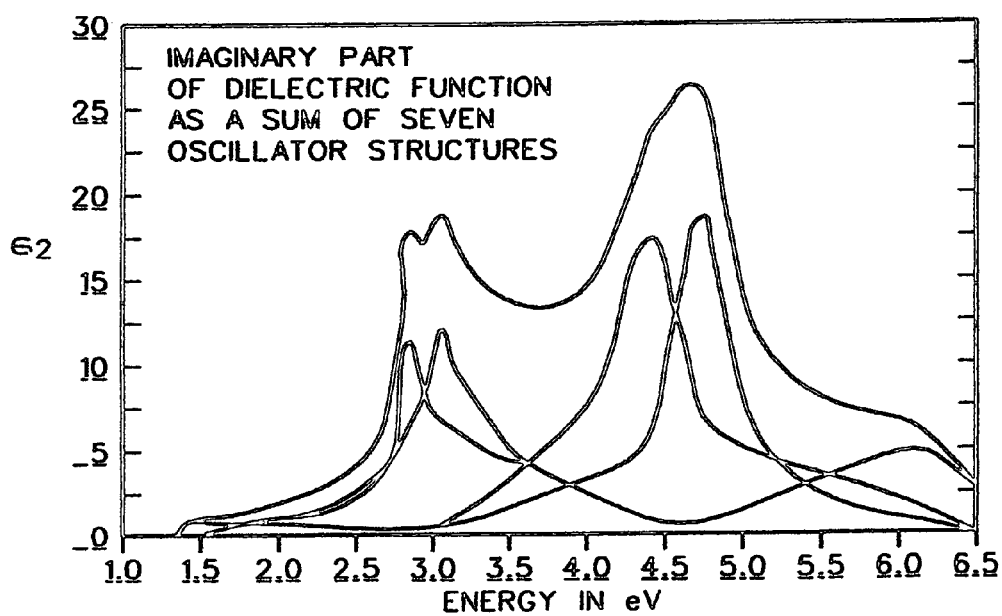
FIG. 6 shows the plot of FIG. 5 with seven (7) Oscillator Structures applied thereto.

Turning now to FIG. 5, there is shown a plot of an actual Gallium-Arsonide Sample System Imaginary Dielectric Function (e2) Component vs. Energy. FIG. 6 shows the plot of FIG. 5 approximated by the Summation of the contributions from seven (7) Oscillator Structures as disclosed in Fugs. 4a–4e, (one of which, (ie. Oscillator Structure #1 in following Table 1), is not readily visible, but is present at the left side of the plot, with an "X" coordinate (EC) of 1.785 ev). FIG. 6 demonstrates the conventional approach to using said Oscillator Structures to fit a Complex Curve. Note that each of the Seven (7) Oscillator Structures is applicable over only portions of the full Energy range in the FIG. 6 plot. The Finite Order Polynomial Coefficient and Finite Magnitude Discontinuity definign Mathematical Model Coefficients, (see infra for definition thereof), which serve to define the seven (7) Oscillator Structures utilized in constructing the Mathematical Model represented in FIG. 6 are provided in Table 1.

Finite Discontinuity Magnitudes, consistant with application of Convolution Integral effected Oscillator Structure Broadening, could be selected as appropriate for determination determination and use in calculation of dependent variable values given independent variable values, which in the above provided example were (e2) vs. Photon Energy.

It is noted at this point that FIG. 6 demonstrates typical Conventional application of the 983 Patent Oscillator Structures to model Dielectric Functions. Such conventional practice strives to obain good fit with a minumum of Oscillator Structures, each of which has an effect over a fairly large energy range and can be difficult to apply, even for experienced practitioners. In comparison, as will be discussed with respect to FIGS. 7–8e, the presently disclosed invention makes use of a multiplicity of short-energy-range effect oscillator Structures to the end that the imaginary part of a Dielectric Function is effectively modeled as a sequence of line segments between adjacent Oscillator Structure Peaks, the shape of said line segments each being determined as a sum of the Oscillator structure components present between said adjacent peaks.

Figure 7:
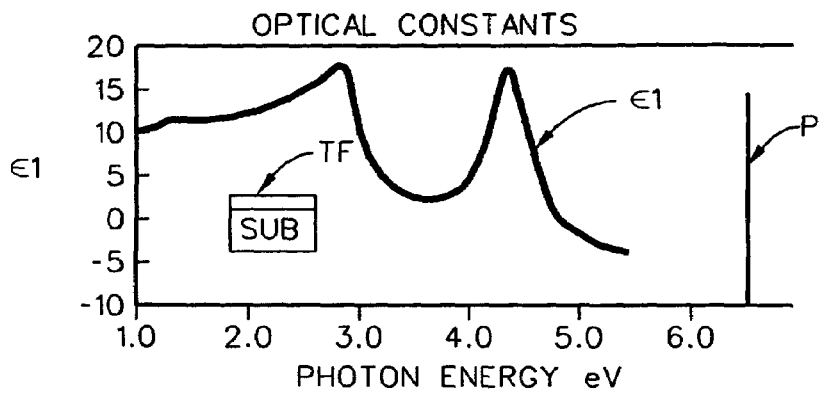
FIG. 7 demonstrates that the real part (e1) of the dielectric function over an energy range of 1 to 6 eV, and demonstrates the presence of a Pole at about 6.5 ev.

Turning now to FIG. 7, which introduces the approach of the presently disclosed invention, it should be noted that it demonstrates that the real part (e1) of the dielectric function over an energy range of 1 to 6 eV, and demonstrates the presence of a Pole at about 6.5 ev. An insert shows that a model for the sample for which the can comprise a substrate

TABLE 1

| # | EL | EU | EC | A | SIGMA | DISC | Lpos | Lamp | L2d | Upos | Uamp | U2d |
|---|----|----|------|-------|-------|------|------|-------|-----|------|------|-----|
| 0 | 0  | 2  | 1.414| 0.43  | 20    | 0.0  | 0.0  | 0.0   | 0   | 0.4  | 0.75 | 0   |
| 1 | 1  | 2  | 1.785| 0.093 | 40    | 0.0  | 0.0  | 0.0   | 0   | 0.4  | 0.75 | 0   |
| 2 | 0  | 4  | 2.896| 11.98 | 33.1  | 0.2  | 0.75 | 0.196 | 1   | 0.8  | 0.4  | 0   |
| 3 | 0  | 4  | 3.17 | 13.19 | 45.28 | 0.1  | 0.3  | 0.03  | 0   | 0.1  | 0.045| 0   |
| 4 | 3  | 6  | 4.64 | 22.38 | 154.1 | 0.36 | 0.4  | 0.136 | 0   | 0.6  | 0.4  | 0   |
| 5 | 3  | 6  | 4.89 | 22.22 | 164.7 | 0.72 | 0.5  | 0.06  | 0   | 0.1  | 0.02 | 0   |
| 6 | 5  | 6  | 6.5  | 5.8   | 200.0 | 0.0  | 0.5  | 0.5   | 0   | 0.0  | 0.0  | 0   |
| 7 | 7  | 7  | 7.195| 50.75 | 0.0   | 0.0  | 0.0  | 0.0   | 0   | 0.0  | 0.0  | 0   |

A Zero-Width Finite Magnitude Pole with a Magnitude of 50.75, present at 7.195 ev, (beyond the range of Energy levels shown in FIG. 6), tabulated in the seventh row of Table 1, was assumed as present to account for all effects caused by unknown data to the right of 6.5 ev. The value of the Magnitude thereof being determined by the parameter evaluation routine which also provided values for the various Finite Order Polynomial Coefficient and Finite Magnitude Discontinuity Magnitudes defining Mathematical Model Coefficients. (Note, a mathematically equivalent result could be effected by use of a Finite Magnitude Discontinuity of 50.75, beginning at at coordinates (0.0, 7.195), rather than by the use of a Zero-Width Oscilator Structure, (ie. a "Pole"), as shown in Table 1).

Comparison of FIGS. 5 and 6 show that the Mathematical Model arrived at by practice of the Method of Use of the Oscillator Structures as applied to the plotted data in FIG. 5, provides a very close replication of said data, as shown in FIG. 6. With that in mind, it is noted that only Oscillator Structure 2, (see Table 1), provides second order Polynomials, (ie. L2d is 1), and that Oscillator Structures #0 and #1 have no associated F1 and F2 Polynomials present. It should be appreciated that the Oscillator Structure Mathematical Model Coefficients identified as determined in Table 1 and FIG. 4a, are arbitrary, and that any Coefficients which allow evaluating present Finite Order Polynomial Coefficients and (SUB) and a Thin Film (TF). The presently disclosed invention teaches that the Thin Film (TF) can be mathematically modeled by a Thickness and, for instance, a Cauchy Dispersion Function and parameters therein, along with Loation and Amplitude for the Pole (P) evaluated by a global regression of said model onto the real part (e1) of the dielectric function data. (See FIG. 4e for insight as to how a Pole can be formed by setting F1, F2, F3 and F4 to zero in FIG. 4a). A first fit step in the presently disclosed invention is then to determine Thin Film (TF) Thickness and parameter values which define the Pole (P) location and amlitude, (which pole accounts for effects at energies higher than a defined energy range of interest).

FIGS. 8a–8f demonstrate the steps of the presently disclosed invention which involve a method of applying a plurality of applying oscillator structures which are formed by variously assigning definition to F1, F2, F3 and F4 in FIG. 4c, (ie. F1 and F4 are assigned to be straight lines, and F2 and F3 set to zero lenght). Note that a similar oscillator structure results from setting F2 and F3 to be straight lines and F1 and F4 to be of zero length, (again see FIG. 4c for the locations of F1, F2, F3 and F4). Other combinations are possbile to provide the same functional result. An example of the resulting oscillator structure can be observed in FIG. 8b, where is shown a triangular shaped sturcture in dashed lines spanning energy 3–5.5 eV with a peak at 4.5 eV. Note that FIG. 8b also shows that additional oscillator structures are located to the right and left of the oscillator centered at 4.5 eV, and that a common theme is that the disclosed oscillator structures begin and/or end where an adjacent oscillator structure peaks. The Triangular Structures formed by the straight lines, (eg. F1 and F4), are each identified by (T). FIGS. 8a and 8b show simple demonstrative imaginary dielectric part (e2) plots which are fit, respectively, by two and three, Triangular SHaped Oscillator Structures (T).

Figure 8C:
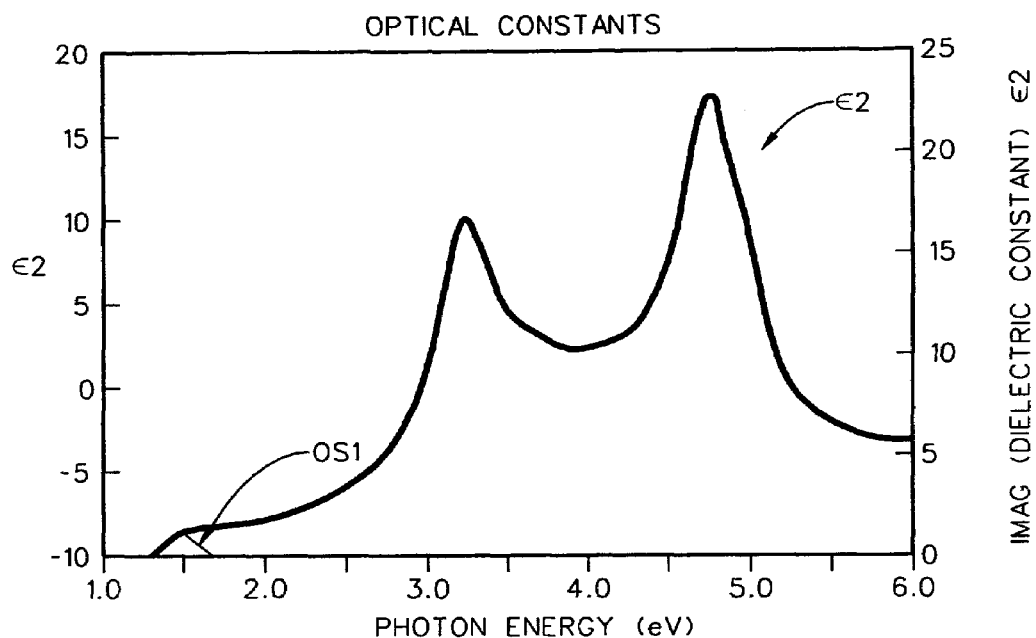
Figure 8D:
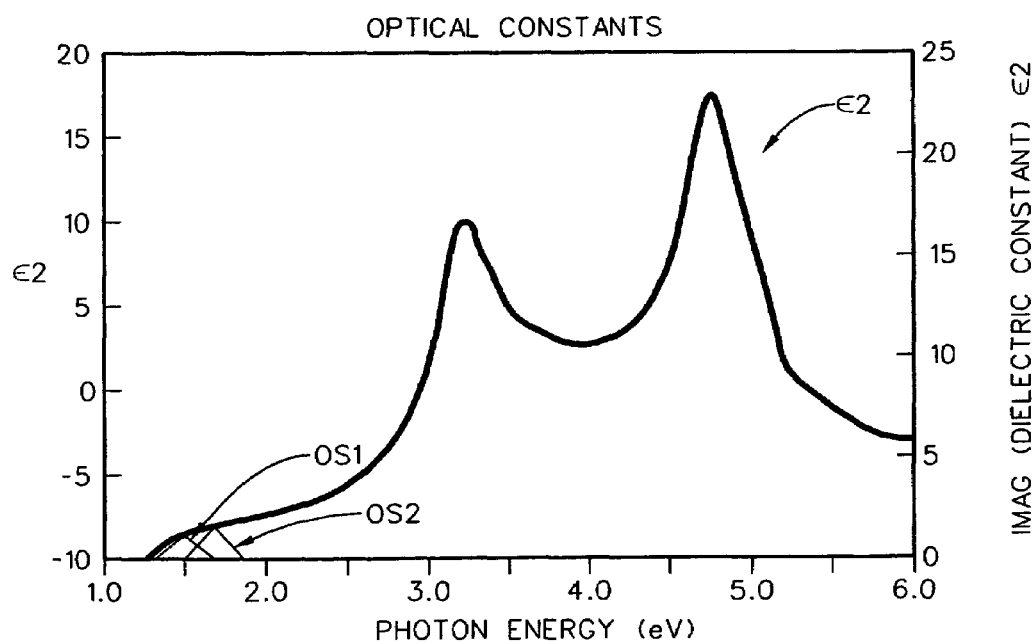
Figure 8E:
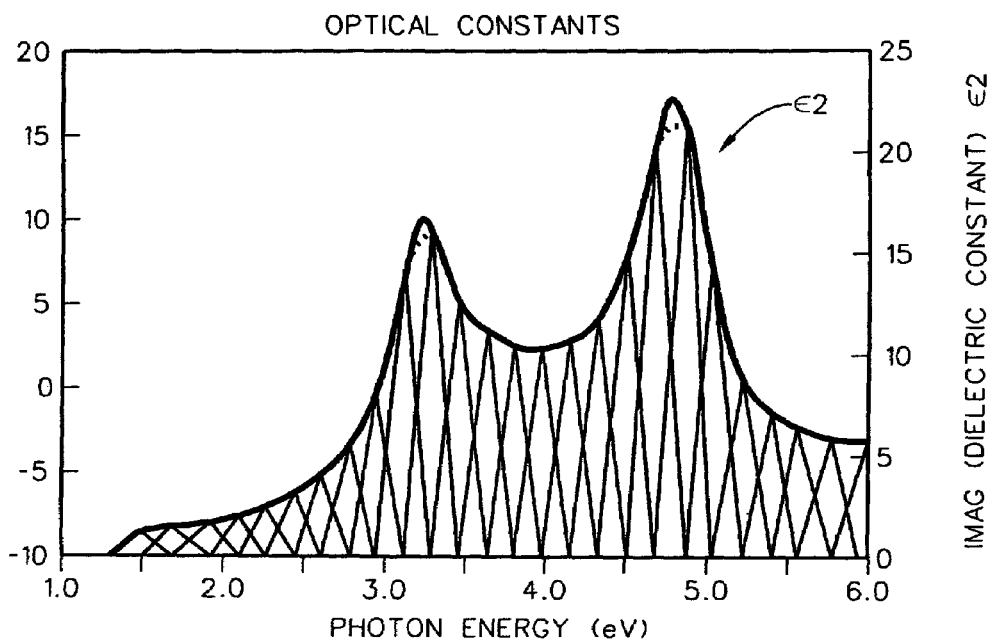
Figure 8F:
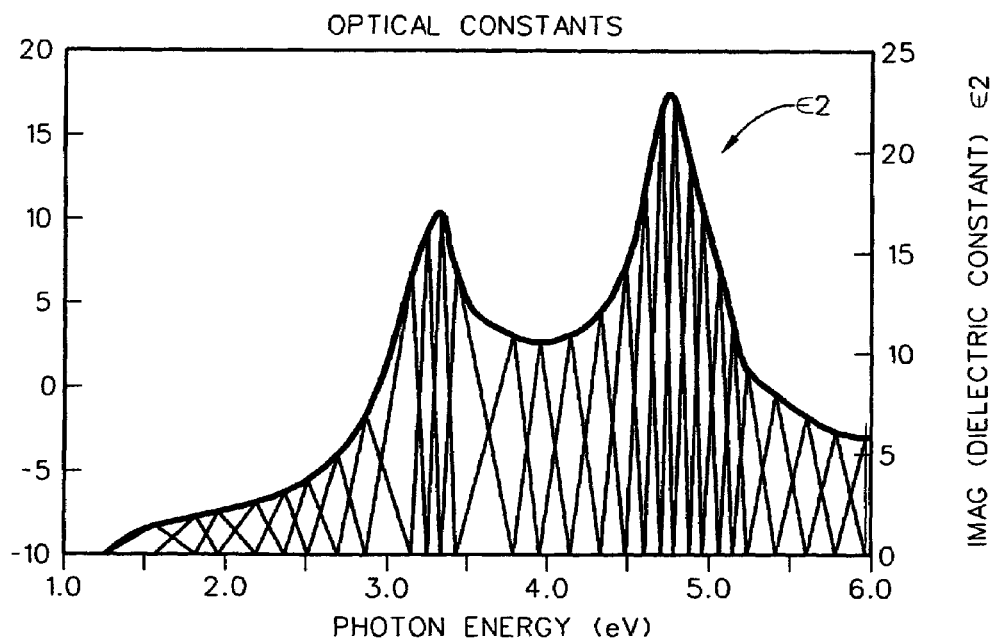

FIGS. 8c and 8d demonstrate application of the method of the presently disclosed invention. FIG. 8c shows a first Oscillator Structure (OS1) applied to fit a left-most portion of a shown imaginary part of a dielectric part (e2), and FIG. 8d shows first and second Oscillator Structures (OS1) applied to fit a bit more of the left-most portion of said shown imaginary dielectric function part (e2). (Note, the procedure could have been started at the right side of the plot and remain within the scope of the disclosed invention). In practice the first Oscillator Structure (OS1) is fit to the data, typically via a point-by-point square error reducing procedure. This is followed by adding the Second Oscillator Structure (OS2) as shown in FIG. 8b, and again performing a fitting procedure which evaluates parameters in said second oscillator structure (OS2) and simultaneously re-evaluates parameters in the first Oscillator Structure (OS1). FIG. 8e demonstrates a result where the point-by-point procedure indicated by FIGS. 8a and 8b is continued over the entire energy range. Note that FIG. 8e assumes that equal energy (ie. wavelength), range segment steps are used for all oscillator structures. It can be observed that this leads to error in peak regions. A modified approach is demonstrated in FIG. 8f, and provides for using variable length wavelength range segments, specifically note the use of smaller energy steps in peak regions. Again, as Oscillator Sturcture are added a fitting procedure is again performed which evaluates parameters in an added oscillator structure and simultaneously re-evaluates parameters in the previously evaluated Oscillator Structure(s).

With all Oscillator Structures evaluated by the point-by-point approach just described, using parameter values as starting values, a global fit can be performed. It is noted that typically the evergy range over which an Oscillator Structure applies is fixed during point-by-point procedures, but in such a global fitting, the base width as well as amplitude of the Oscillator Structures can be allowed to float. Further, while the point-by-point fits are onto data representing the imaginary part of the Dielectric Function, the Global fit can be onto data representing both real and imaginary parts of thereof.

Figure 8G:
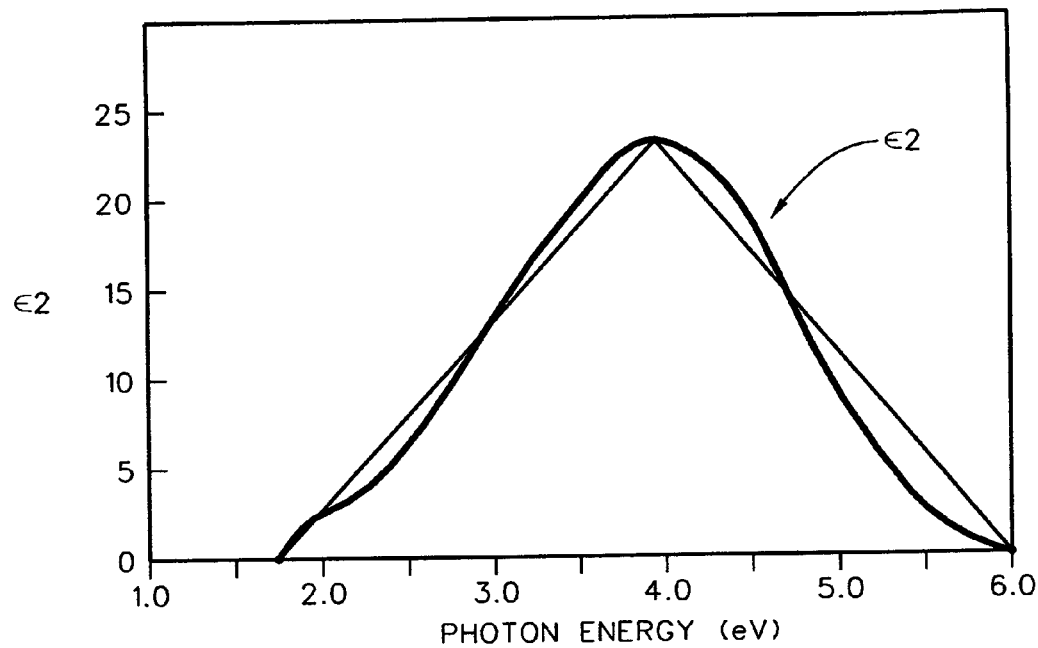
Figure 8H:
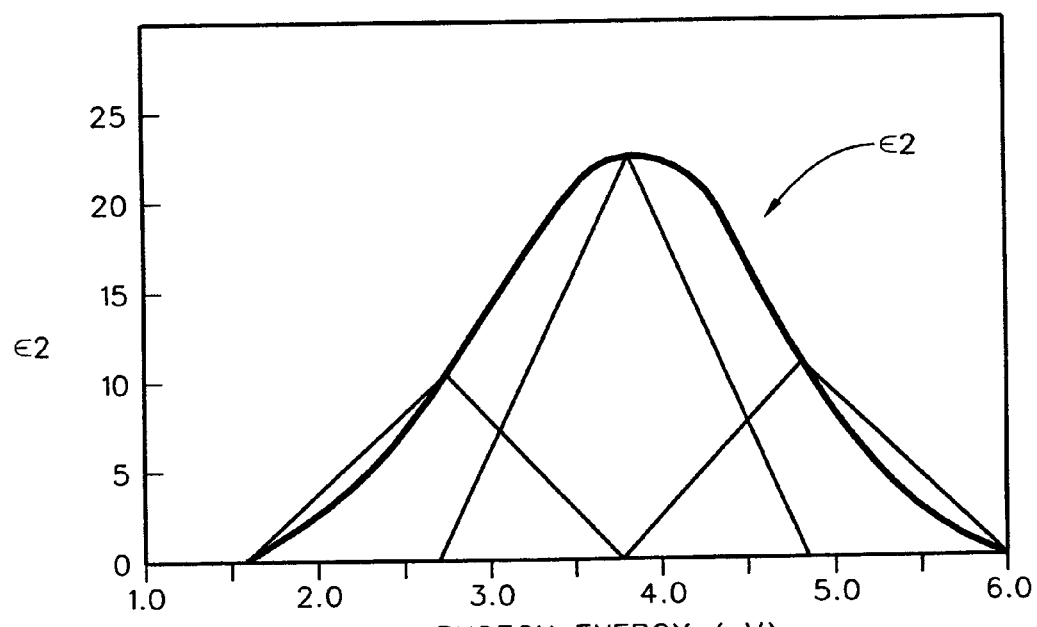
Figure 8I:
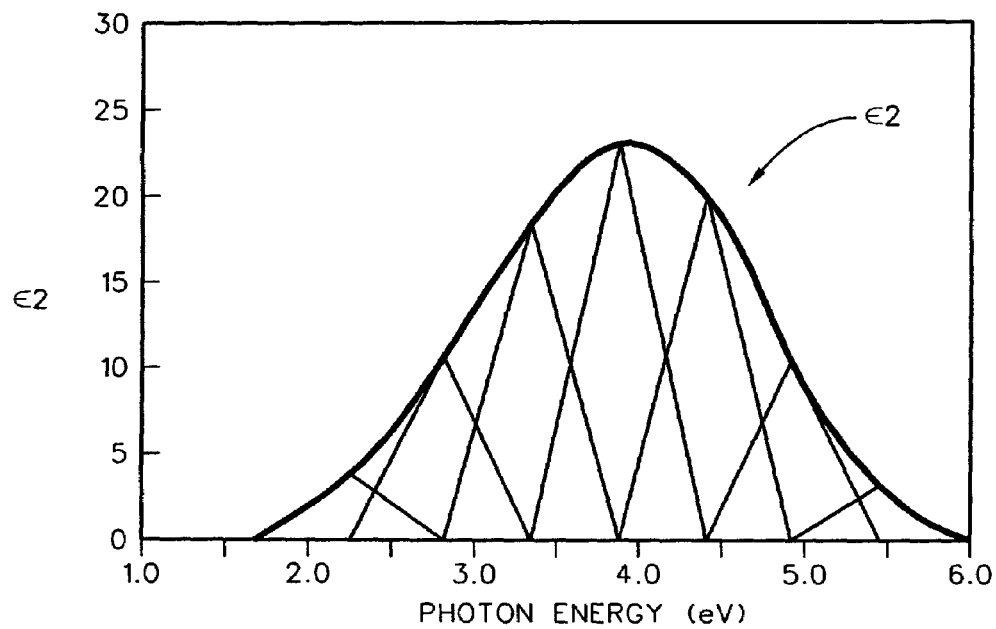
Figure 8J:
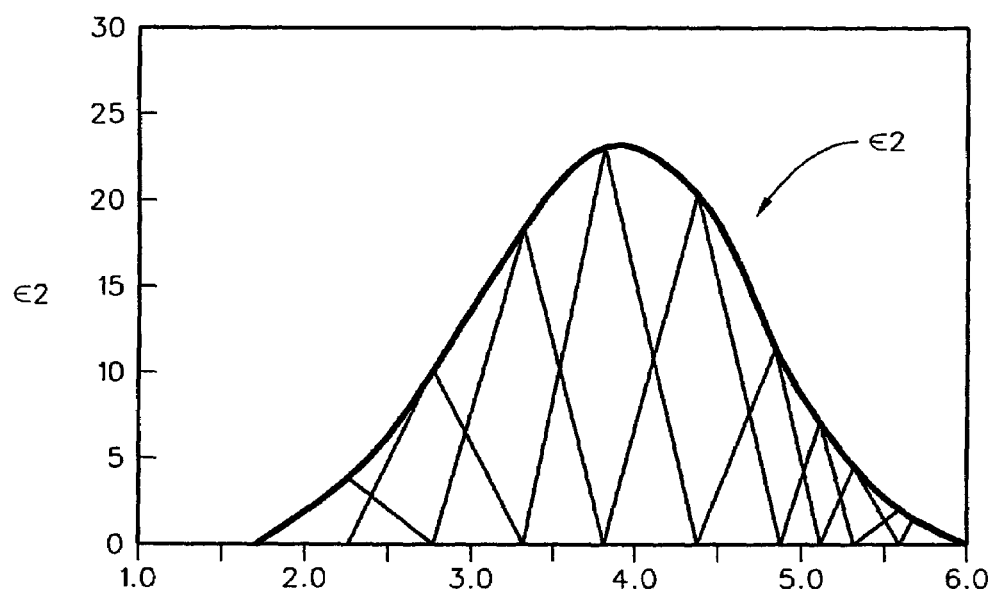

FIGS. 8g–8j demonstrate that the approach to assigning oscillator structures can involve beginning at a central location and specifying some number of segments. FIG. 8g speficies one segment, while FIGS. 8h and 8i specified two and four equal length segments respectively. FIG. 8j shows five specified segments, wherein the last two are shorter than the first three. Note that where two segments are specified, three oscillator structures are present. FIG. 8i shows that where four segments are present, seven oscillator structures are present and FIG. 8j shows that where five segments are present nine oscillators are present. This occurs based on the method of positioning the oscillator structures such that sequentially, each successive oscillator structure begins where the just prior oscillator structure peaks. Typically global fitting will be applied in such a scenario.

Figure 8K:
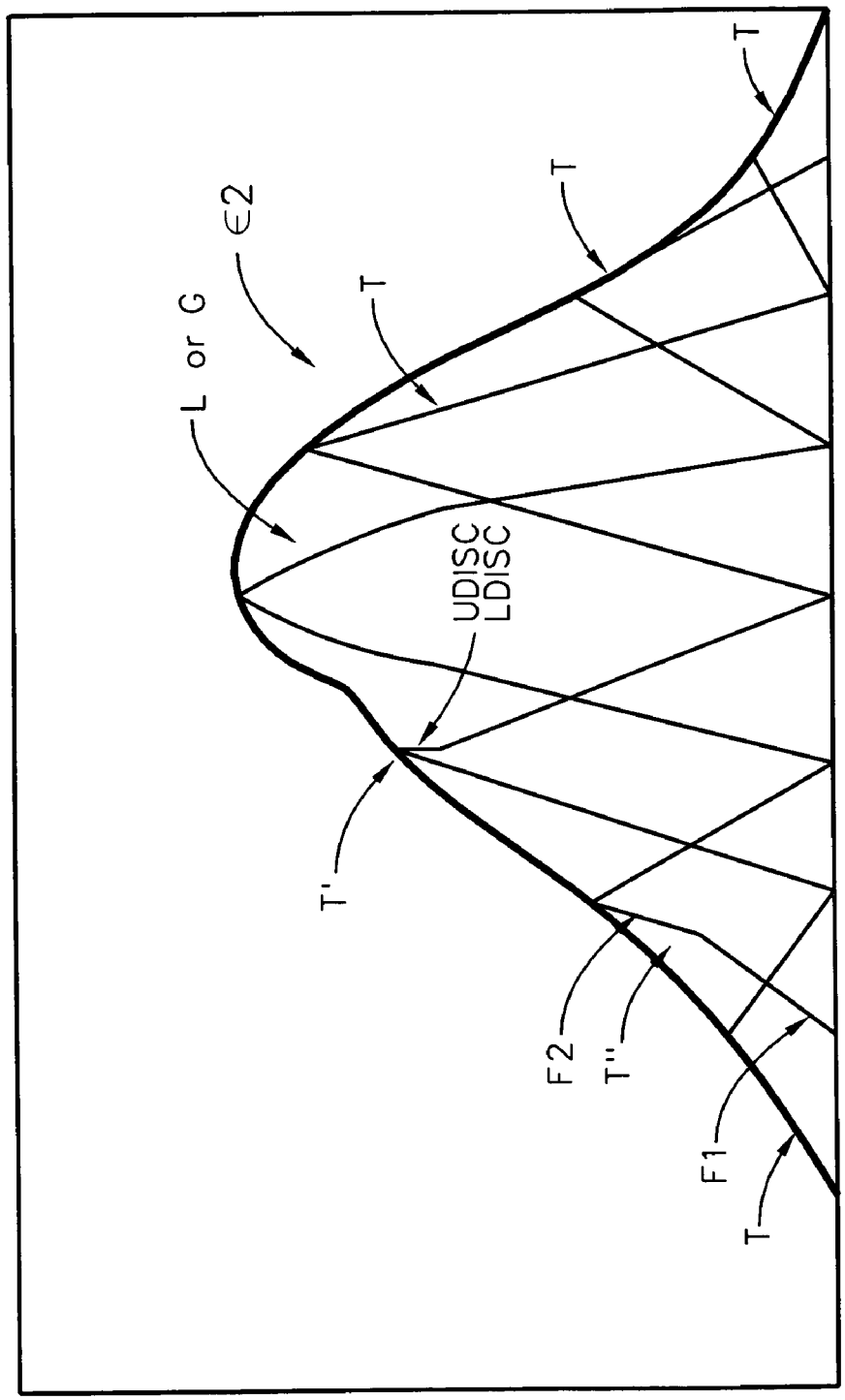
FIG. 8k shows use of one Gaussian or Narrow Lorentz (G or L), five Triangular (T), and two modified triangular (T') (T") shaped Oscillator Structures.

FIG. 8k shows use of one Gaussian or Narrow Lorentz (G or L), five Triangular (T), and two Modified Triangular (T') (T") shaped Oscillator Structures. Note that Modified Triangular Shaped Oscillator (T') includes Discontinuies (UDISC) (LDISC), and that Modified Triangular Shaped Oscillator (T") is constructed from a polynomial (F1) and a straight line segment (F2). FIG. 8 is included to demonstrate that while triangular (T) shaped oscillators are preferred, the present invention methodology allows for use of different functional Oscillator Structures in modeling a dilectric function. A requirement of all Oscillator Structures is, however, that definite start and end point intersections with the horizontal axis must be identifiable so that generally the start and end points of one oscillator can be positioned directly beneath the peak of the Oscillator Structures directly adjacent thereto. It is pointed out that the start and end of the first and last Oscillator Structure, of course, have no adjacent Oscillator Structure peak positioned thereabove.

Figure 4K:
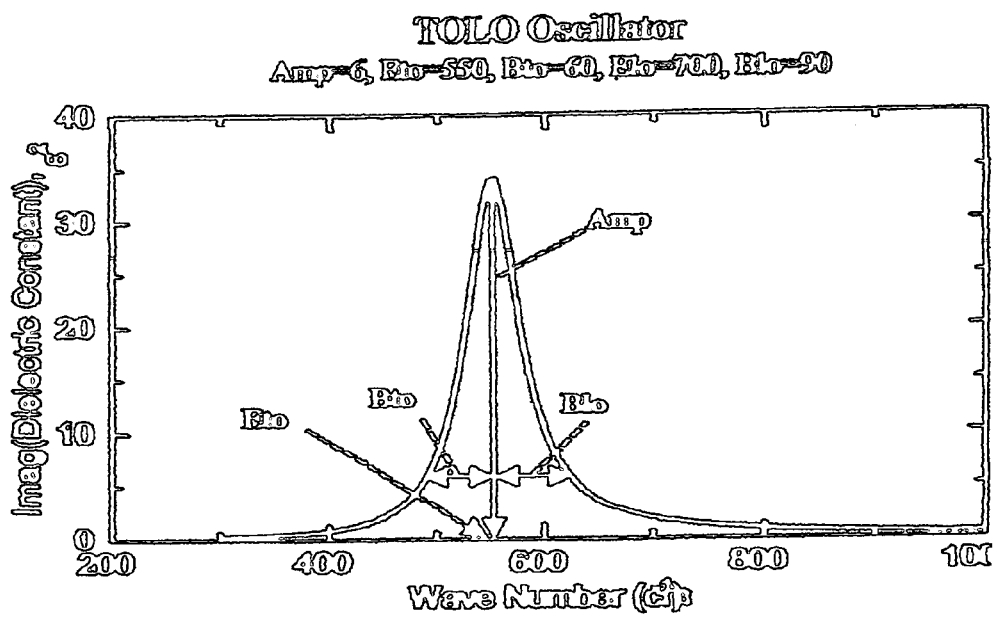

It is emphasised that while, for simplicity, Triangular shaped Oscillator Structures are shown in FIGS. 8a–8j, any functional shape Oscillator Structures such as shown in FIGS. 4c and 4f–4j can be applied, and it is possible to apply more than one type, (eg, mixed Traingular and/or Modified Triangular and Gaussian and/or Narrow Lorentz and/or Harmonic and/or Triangular and/or TOLO etc., see FIG. 4k for an example). The novel requirement is that the segmental modeling of imaginary parts of dielectric functions is with Oscillator Structures that have substantially starting and ending points and which are Kramers-Kronig (K-K) consistent be achieved.

It is be understood that while Dielectric Functions are recited in the claims, Refractive Index and Extinction Coefficient Optical Constants are mathematically equivalent and in that light are within the scope thereof.

It is also to be understood that the terminology "Pole" can include functional equivalents to zero width structures. For instance, very narrow oscillators with finite amplitudes are within the scope of "Pole".

It is also to be understood that providing experimentally obtained data for real and imaginary parts of a dielectric function vs. wavelength for a sample comprising a transparent thin film on a substrate, over a determined range of wavelengths can involve providing equivalent ellipsometric PSI and ellipsometric DELTA data.

It is to be understood that Dielectric Function vs. Photon Energy data used in the practice of the Method of the present invention can be obtained by Ellipsometry, and by any other applicable technique, such as Transmission and Reflectance.

Having hereby disclosed the subject matter of the present invention, it should be obvious that many modifications, substitutions, and variations of the present invention are possible in light of the teachings. It is to be understood that the invention can be practiced other than as specifically described, and should be limited in breadth and scope only by the claims.

We claim:

1. A method of segmentally modeling real and imaginary parts of dielectric functions with Kramers-Kronig (K-K) consistent oscillators, comprising the steps of:
   practicing steps a and b:
   a) providing experimentally obtained data for real and imaginary parts of a dielectric function vs. wavelength, which characterize a sample comprising a transparent thin film on a substrate, over a determined range of wavelengths;
   b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a global fitting procedure evaluating parameters, including the thickness of the transparent thin film and the location and amplitude of the pole in said mathematical model, utilizing the data corresponding to the real part of the dielectric function;

with transparent thin film thickness evaluated in step b, proceeding to practice steps c and d sequentially:

c) defining a wavelength range segment length and selecting an integer n such that the sum of n+0.5 wavelength range segments exactly span the determined wavelength range, and beginning at one end of said determined wavelength range placing a K-K consistent oscillator which comprises an amplitude parameter and begins and ends at the extents of the first segment with its peak midway therebetween, then performing a point by point fit to the imaginary part of the dielectric function data over wavelengths in said first wavelength range segment such that K-K consistent oscillator defining parameters are evaluated;

d) placing a second K-K consistent oscillator which begins at a wavelength at which the first K-K consistent oscillator peaks and ends one wavelength range segment length therefrom and has a peak midway therebetween, then performing a point by point fit to the imaginary part of the dielectric function data over said first and second wavelength range segments such that K-K consistent oscillator defining parameters in said first K-K consistent oscillator are re-evaluated and oscillator defining parameters in said second K-K consistent oscillator are evaluated; and for each of the remaining n−2 wavelength range segments, sequentially practicing step e;

e) placing a K-K consistent oscillator which begins at a wavelength at which the just prior K-K consistent oscillator peaks and ends one wavelength range segment length therefrom and having a peak midway therebetween, then performing a point by point fit to the imaginary part of the dielectric function data over said wavelength range segments which are fitted with K-K consistent oscillators, such that oscillator defining parameters in previously evaluated K-K consistent oscillators are re-evaluated and oscillator defining parameters in the added oscillator are evaluated, with the result being that at each wavelength over the determined range of wavelengths the sum of the contributions of each evaluated K-K consistent oscillator approximates the magnitude of the imaginary part of the dielectric function.

2. A method as in claim 1, in which at least one K-K consistent oscillator is of a shape selected from the group consisting of:
Gaussian;
Lorentzian;
Harmonic;
Ionic1;
Ionic2; and
TOLO.

3. A method as in claim 2, in which the global and point by point fits are based on a square error minimization criteria.

4. A method as in claim 1, which further comprises step f:

f) using starting values of parameters previously evaluated performing a global fitting procedure onto both real and imaginary parts of the dielectric function to re-evaluate parameters, including the thickness of the transparent thin film, the location and amplitude of the pole in said mathematical model, and K-K consistent oscillator defining parameters utilizing the data corresponding to the real and imaginary parts of the dielectric function, with a constraining limitation that said pole location is required to remain located at a wavelength beyond the lower wavelength, high energy, extent of said determined range of wavelengths.

5. A method as in claim 4 in which, for each of the n wavelength range segments, the segment length thereof is allowed to float and be fit, with required constraints being:
that the sum of all the resulting n+½(n+1) segment lengths remains equal to the length of the determined wavelength range, and
that for the 2nd–nth K-K consistent oscillator each successive K-K consistent oscillator begins at a wavelength at which the immediately preceding n−1 K-K consistent oscillator peaks.

6. A method as in claim 1, in which the global and point by point fits are based on a square error minimization criteria.

7. A method as in claim 6, in which the global and point by point fits are based on a square error minimization criteria.

8. A method as in claim 1, in which the pole location and its amplitude at a wavelength beyond the lower wavelength, high energy, extent of said determined range of wavelengths, are fixed during steps c, d and e.

9. A method as in claim 1, in which both the data real and imaginary parts the dielectric function data are fitted, and the pole location and/or its amplitude are re-evaluated along with previously evaluated oscillator defining parameters in previously evaluated K-K consistent oscillators during steps c, d and e, but wherein said pole location is required to remain located at a wavelength beyond the lower wavelength, high energy, extent of said determined range of wavelengths.

10. A method as in claim 1, in which at least one K-K consistent oscillator is of tiangular shape.

11. A method as in claim 1, in which at least one K-K consistent oscillator is constructed from at least one polynomial on at least one side of the peak value thereof.

12. A method of segmentally modeling real and imaginary parts of dielectric functions with Kramers-Kronig (K-K) consistent oscillators, comprising the steps of:
practicing steps a and b:
a) providing experimentally obtained data for real and imaginary parts of a dielectric function vs. wavelength, which characterize a sample comprising a transparent thin film on a substrate, over a determined range of wavelengths;
b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a global fitting procedure evaluating parameters, including the thickness of the transparent thin film and the location and amplitude of the pole in said mathematical model, utilizing the data corresponding to the real part of the dielectric function;

with transparent thin film thickness evaluated in step b, proceeding to practice steps c and d sequentially:

c) defining n wavelength range segment lengths such that the sum of said n wavelength range segment lengths plus half the length of the last wavelength range segment at one end of said wavelength range exactly spans the determined wavelength range, and beginning at the opposite end of said determined wavelength range placing a K-K consistent oscillator which comprises an amplitude parameter and begins and ends at the extents of the first segment with its peak midway therebetween, then performing a point by point fit to the imaginary part of the dielectric function data over wavelengths in said first wavelength range segment such that K-K consistent oscillator defining parameters are evaluated;

d) placing a second K-K consistent oscillator which begins at a wavelength at which the first K-K consistent oscillator peaks and ends at the second wavelength range segment length therefrom and has a peak midway therebetween, then performing a point by point fit to the imaginary part of the dielectric function data over said first and second wavelength range segments such that K-K consistent oscillator defining parameters in said first K-K consistent oscillator are re-evaluated and oscillator defining parameters in said second K-K consistent oscillator are evaluated; and for each of the remaining n–2 wavelength range segments, sequentially performing step e;

e) placing a K-K consistent oscillator which begins at a wavelength at which the immediately preceeding K-K consistent oscillator peaks and ends at the nth wavelength range segment length therefrom and having a peak midway therebetween, then performing a point by point fit to the imaginary part of the dielectric function data over said wavelength range segments which are fitted with K-K consistent oscillators, such that oscillator defining parameters in previously evaluated K-K consistent oscillators are re-evaluated and oscillator defining parameters in the added oscillator are evaluated, with the result being that at each wavelength over the determined range of wavelengths the sum of the contributions of each evaluated K-K consistent oscillator approximates the magnitude of the imaginary part of the dielectric function.

13. A method as in claim 12, in which at least one K-K consistent oscillator is constructed from at least one polynomial on at least one side of the peak value thereof.

14. A method as in claim 13 in which, for each of the n the wavelength range segments, the segment length thereof is allowed to float and be fit with required constraints being:

that the sum of all the resulting n+½ (n+1) segment lengths remains equal to the length of the determined wavelength range, and that for the 2nd–nth K-K consistent oscillator each successive K-K consistent oscillator begins at a wavelength at which the immediately preceeding n–1 K-K consistent oscillator peaks.

15. A method as in claim 14 in which the global and point by point fits are based on a square error minimization criteria.

16. A method as in claim 12 which further comprises step f:

f) using starting values of parameters previously evaluated performing a global fitting procedure onto both real and imaginary parts of the dielectric function to re-evaluate parameters, including the thickness of the transparent thin film, the location and amplitude of the pole in said mathematical model, and the K-K consistent oscillator defining parameters utilizing the data corresponding to the real and imaginary parts of the dielectric function, with a constraining limitation that said pole location is required to remain located at a wavelength beyond the lower wavelength, high energy, extent of said determined range of wavelengths.

17. A method as in claim 16, in which the global and point by point fits are based on a square error minimization criteria.

18. A method as in claim 12 in which the pole location and its amplitude at a wavelength beyond the high energy extent of said determined range of wavelengths, are fixed during steps c, d and e.

19. A method as in claim 12, in which both the data real and imaginary parts the dielectric function data are fitted, and the pole location and/or its amplitude are re-evaluated along with previously evaluated oscillator defining parameters in previously evaluated K-K consistent oscillators during steps c, d and e, but wherein said pole location is required to remain located at a wavelength beyond high energy extent of said determined range of wavelengths.

20. A method as in claim 12, in which at least one K-K consistent oscillator is of tiangular shape.

21. A method as in claim 12, in which at least one K-K consistent oscillator is of a shape selected from the group consisting of:

Gaussian;
Lorentzian;
Harmonic;
Ionic1;
Ionic2; and
TOLO.

22. A method as in claim 12, in which the global and point by point fits are based on a square error minimization criteria.

23. A method of segmentally modeling real and imaginary parts of dielectric functions with Kramers-Kronig (K-K) consistent oscillators, comprising the steps of:

practicing steps a and b:

a) providing experimentally obtained data for real and imaginary parts of a dielectric function vs. wavelength, which characterize a sample comprising a transparent thin film on a substrate, over a determined range of wavelengths;

b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a fitting procedure evaluating parameters, including the transparent thin film thickness and the location and amplitude of the pole in said mathematical model, utilizing the data corresponding to the real part of the dielectric function;

with transparent thin film thickness evaluated in step b, proceeding to practice step c:

c) defining a wavelength range segment length and selecting an integer n such that the sum of n wavelength range segments exactly span the determined wavelength range, and beginning centrally in said determined wavelength range placing a first K-K consistent oscillator which comprises an amplitude parameter and begins and ends at the extents of the first segment with its peak midway therebetween; and for each of the remaining n–1 wavelength range segments, on both sides of the central peak of the first K-K consistent oscillator practicing steps d and e;

d) placing a K-K consistent oscillator which begins at a wavelength at which the just centrally prior K-K consistent oscillator peaks and ends one wavelength range segment length therefrom and having a peak midway therebetween;

e) performing a fit to the imaginary part of the dielectric function data over said wavelength range segments which are fitted with K-K consistent oscillators, such that oscillator defining parameters in the K-K consistent oscillators are evaluated;

such that at each wavelength over the determined range of wavelengths the sum of the contributions of each evaluated K-K consistent oscillator approximates the magnitude of the imaginary part of the dielectric function.

24. A method as in claim 23 in which the pole location and its amplitude at a wavelength beyond the high energy extent of said determined range of wavelengths, are fixed during step e.

25. A method as in claim 23, in which both the real and imaginary parts the dielectric function data are fitted, and the pole location and/or its amplitude are re-evaluated along with previously evaluated oscillator defining parameters in the K-K consistent oscillators during step e, but wherein said pole location is required to remain located at a wavelength beyond the high energy extent of said determined range of wavelengths.

26. A method as in claim 23, in which at least one K-K consistent oscillators is of tiangular shape.

27. A method as in claim 23, in which at least one K-K consistent oscillator is constructed from at least one polynomial on at least one side of the peak value thereof.

28. A method as in claim 23, in which at least one K-K consistent oscillator is of a shape selected from the group consisting of:
  Gaussian;
  Lorentzian;
  Harmonic;
  Ionic1;
  Ionic2; and
  TOLO.

29. A method as in claim 23, in which the fits are based on a square error minimization criteria.

30. A method as in claim 23, in which n=1 and the enabling criteria for practicing step d is not met.

31. A method of segmentally modeling real and imaginary parts of dielectric functions with Kramers-Kronig (K-K) consistent oscillators, comprising the steps of:

practicing steps a and b:

a) providing experimentally obtained data for real and imaginary parts of a dielectric function vs. wavelength, which characterize a sample comprising a transparent thin film on a substrate, over a determined range of wavelengths;

b) providing a mathematical model of said sample which comprises a parameter coresponding to the thickness of the transparent thin film and comprises parameters corresponding to a pole amplitude and location at a wavelength beyond the lower wavelength, high energy, extent of said determined range of wavelengths, then by a fitting procedure evaluating parameters, including the thickness of the transparent thin film and the location and amplitude of the pole in said mathematical model, utilizing the data corresponding to the real part of the dielectric function;

with transparent thin film thickness evaluated in step b, proceeding to practice step c:

c) defining n wavelength range segment lengths such that the sum of said n wavelength range segments exactly span the determined wavelength range, and beginning centrally in said determined wavelength range placing a first K-K consistent oscillator which comprises an amplitude parameter and begins and ends at the extents of the first segment with its peak midway therebetween; and for each of the remaining n–1 wavelength range segments, on both sides of the central peak of the first K-K consistent oscillator practicing steps d and e;

d) placing a K-K consistent oscillator which begins at a wavelength at which the just centrally prior K-K consistent oscillator peaks and ends one wavelength range segment length therefrom and having a peak midway therebetween;

e) performing a fit to the imaginary part of the dielectric function data over said wavelength range segments which are fitted with K-K consistent oscillators, such that oscillator defining parameters in the K-K consistent oscillators are evaluated, with the result being that at each wavelength over the determined range of wavelengths the sum of the contributions of each evaluated K-K consistent oscillator approximates the magnitude of the imaginary part of the dielectric function.

32. A method as in claim 31 in which the pole location and its amplitude at a wavelength beyond the high energy extent of said determined range of wavelengths, are fixed during step e.

33. A method as in claim 31, in which both the real and imaginary parts the dielectric function data are fitted, and the pole location and/or its amplitude are re-evaluated along with previously evaluated oscillator defining parameters in the K-K consistent oscillators during step e, but wherein said pole location is required to remain located at a wavelength beyond the high energy extent of said determined range of wavelengths.

34. A method as in claim 31, in which at least one K-K consistent oscillators is of tiangular shape.

35. A method as in claim 31, in which at least one K-K consistent oscillator is constructed from at least one polynomial on at least one side of the peak value thereof.

36. A method as in claim 31, in which at least one K-K consistent oscillator is of a shape selected from the group consisting of:
  Gaussian;
  Lorentzian;
  Harmonic;
  Ionic1;
  Ionic2; and
  TOLO.

37. A method as in claim 31, in which the fits are based on a square error minimization criteria.

38. A method as in claim 31, in which n=1 and the enabling criteria for practicing step d is not met.

39. A method of segmentally modeling real and imaginary parts of dielectric functions with Kramers-Kronig (K-K) consistency, comprising the steps of:
  a) providing an imaginary part of a dielectric function over spectroscopic range, and dividing said spectroscopic range into a plurality of equal length segments;
  b) fitting each and every said segment in said spectroscopic range with an approximating K-K consistent oscillator structure, said approximating oscillator structure in each said segment beginning and ending at the start and end of said segment to which it is fit, such that a summation of contributions from said oscillator structures present at each point within said spectroscopic range approximates said imaginary part of said dielectric function, and because of the K-K consistency the real part of the dielectric function is also approximated.

40. A method as in claim 39, in which the segments are of equal spectroscopic range lengths and at least one of said K-K consistent oscillator structures is triangular shaped.

41. A method as in claim 39, in which the segments are overlapping in that the start and end of all oscillator structures, except the start of the first and end of the last, are positioned at the same spectroscopic points as are peaks of immediately adjacent oscillator structures.

\* \* \* \* \*